US011529146B1

(12) United States Patent
Reydel

(10) Patent No.: US 11,529,146 B1
(45) Date of Patent: Dec. 20, 2022

(54) ENDOSCOPIC CLIP DEVICES AND RELATED METHODS FOR MUCOSAL DEFECT AND TRANSMURAL PERFORATION CLOSURE

(71) Applicant: INVENTIO LLC, West Caldwell, NJ (US)

(72) Inventor: Boris Reydel, West Caldwell, NJ (US)

(73) Assignee: INVENTIO LLC, West Caldwell, NJ (US)

( * ) Notice: Subject to any disclaimer, the term of this patent is extended or adjusted under 35 U.S.C. 154(b) by 0 days.

(21) Appl. No.: 17/830,326

(22) Filed: Jun. 1, 2022

Related U.S. Application Data

(60) Provisional application No. 63/258,814, filed on Jun. 1, 2021.

(51) Int. Cl.
*A61B 17/122* (2006.01)
*A61B 17/128* (2006.01)
*A61B 17/00* (2006.01)
*A61B 17/12* (2006.01)

(52) U.S. Cl.
CPC ........ *A61B 17/122* (2013.01); *A61B 17/1285* (2013.01); *A61B 2017/0034* (2013.01); *A61B 2017/00818* (2013.01); *A61B 2017/12004* (2013.01)

(58) Field of Classification Search
CPC ............ A61B 17/1285; A61B 17/1227; A61B 17/083; A61B 17/122; A61B 2017/0034; A61B 2017/12004; A61B 2017/00818
See application file for complete search history.

(56) References Cited

U.S. PATENT DOCUMENTS

2021/0330327 A1\* 10/2021 Saenz Villalobos ........................ A61B 17/083
2022/0096088 A1\* 3/2022 Sato ..................... A61B 17/122

\* cited by examiner

*Primary Examiner* — Majid Jamialahmadi
(74) *Attorney, Agent, or Firm* — Meunier Carlin & Curfman LLC

(57) ABSTRACT

An endoscopic clip device for closure of a mucosal defect or transmural perforation in a gastrointestinal wall may include a sleeve and a clip disposed at least partially within and coupled to the sleeve. The clip may be configured for reversibly moving between an open configuration for positioning relative to the wall and a closed configuration for closing the defect or perforation. The clip may include a first clip arm configured for engaging the mucosal and submucosal layers of the wall and including a first needle extending to a distal end of the first clip arm and configured for advancing through the mucosal layer and into at least the submucosal layer, and a second clip arm disposed opposite the first clip arm and configured for engaging the mucosal layer. The device may be configured for advancing through an operative channel of an endoscope or overtube having a tortuous shape.

18 Claims, 20 Drawing Sheets

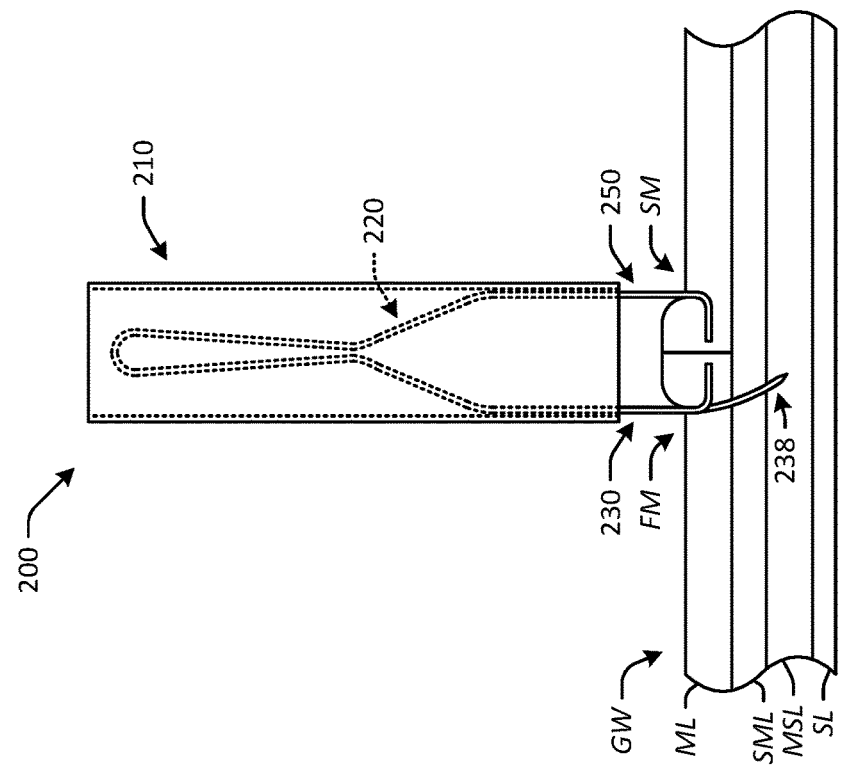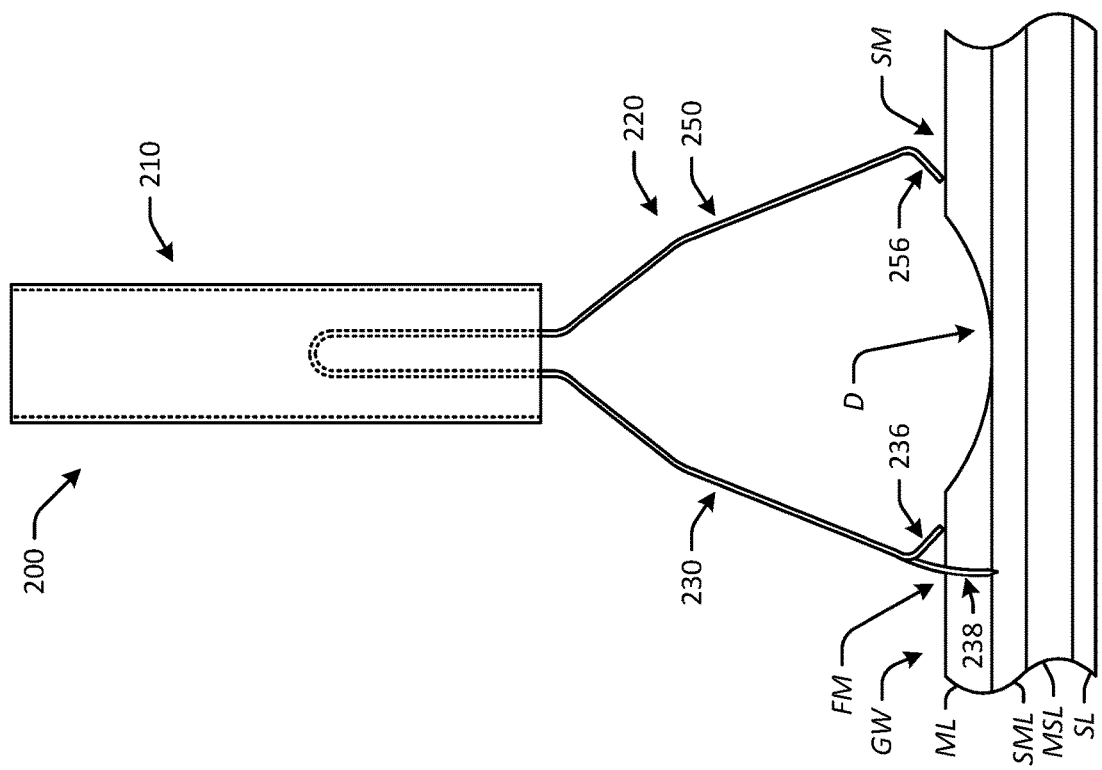

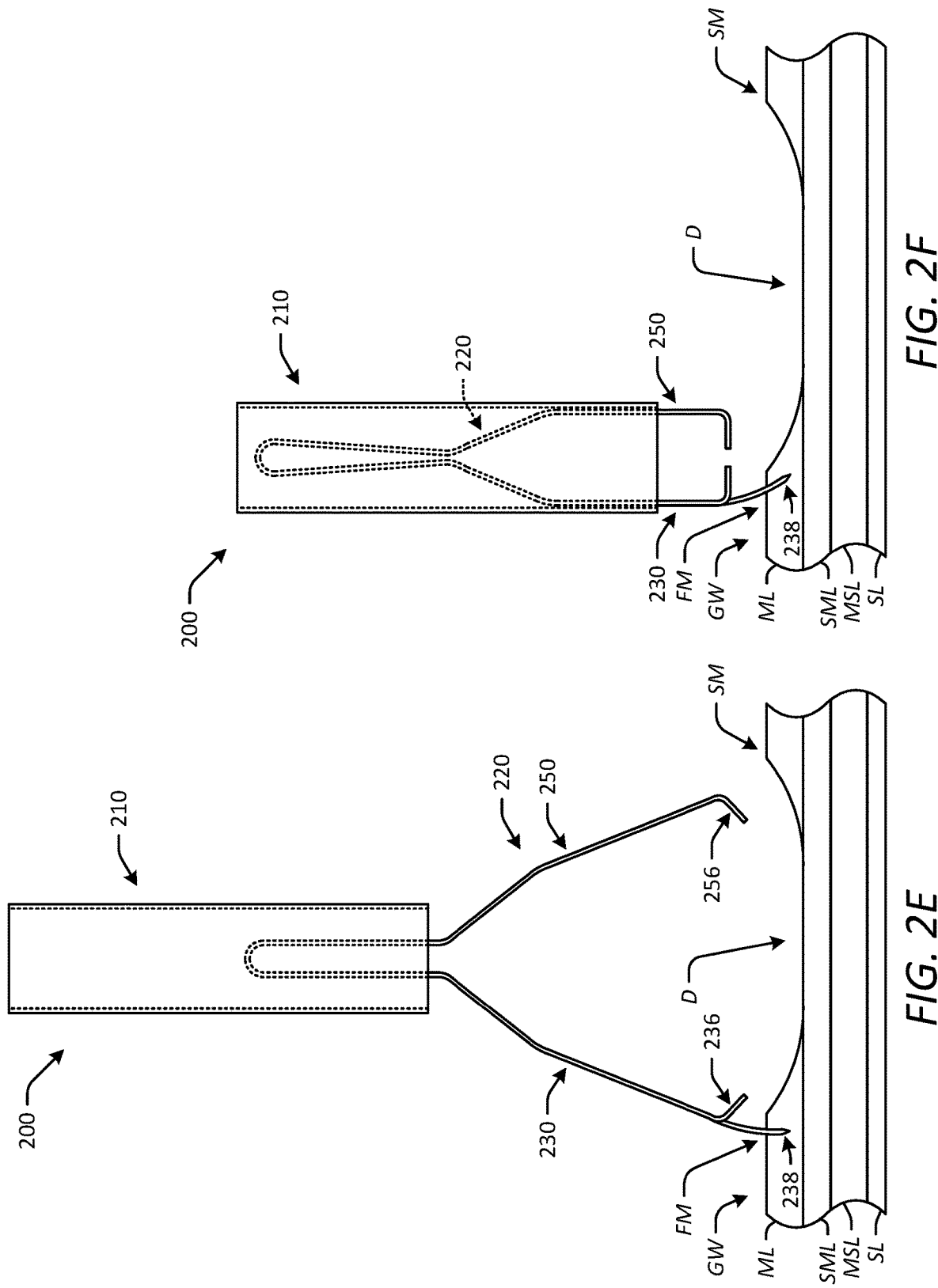

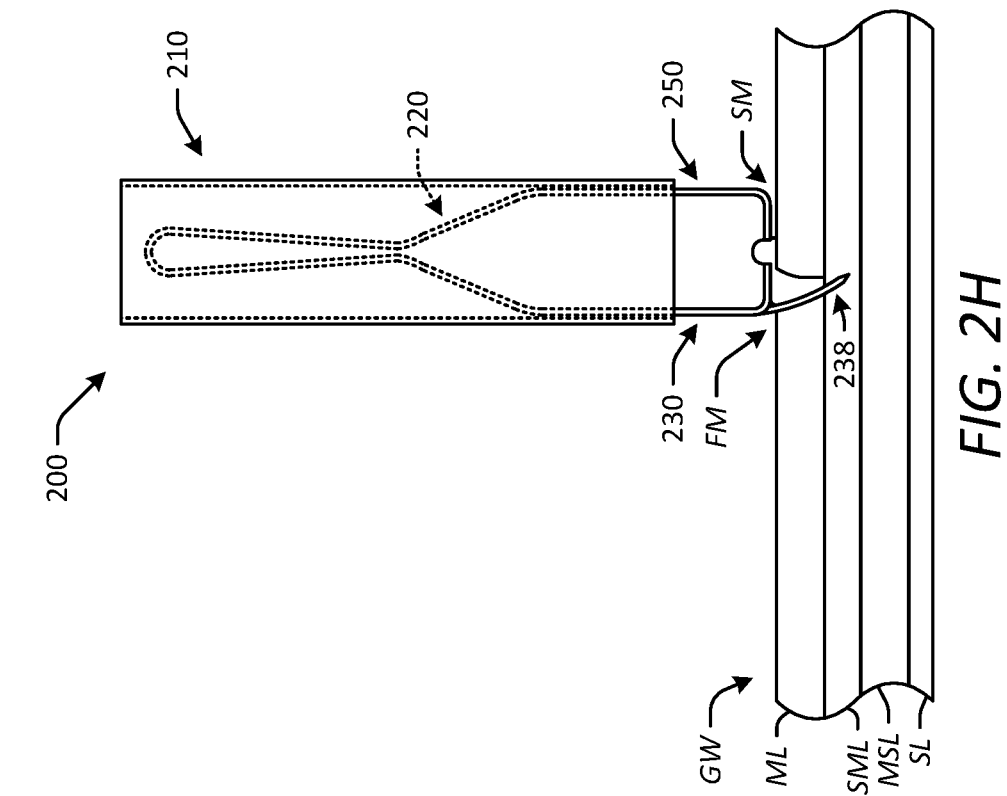
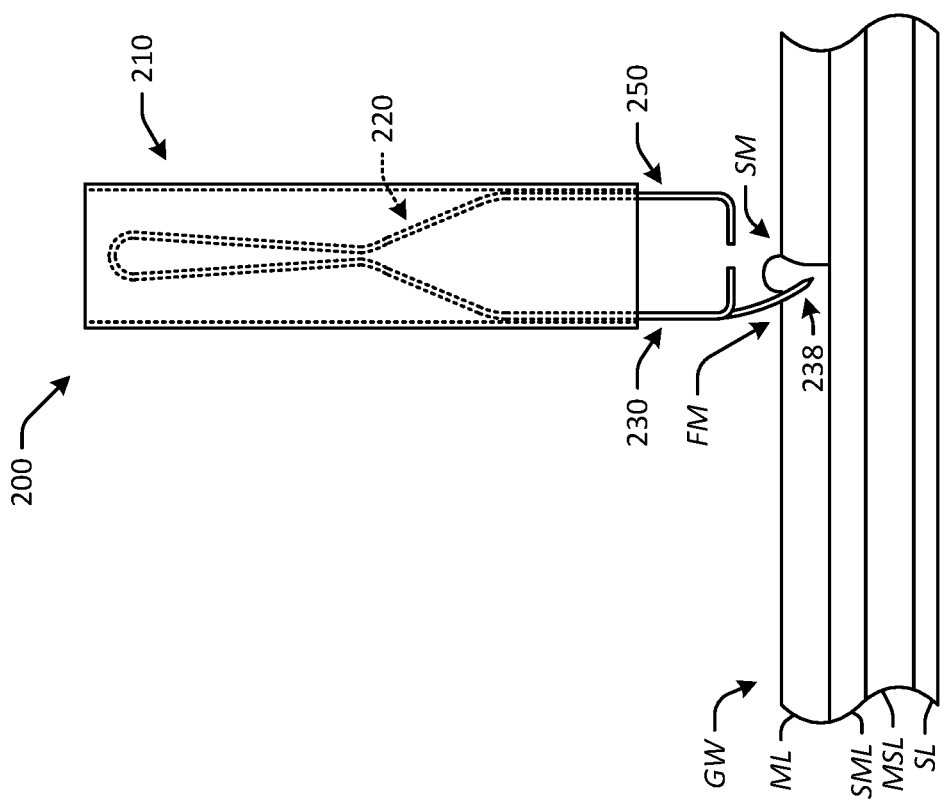

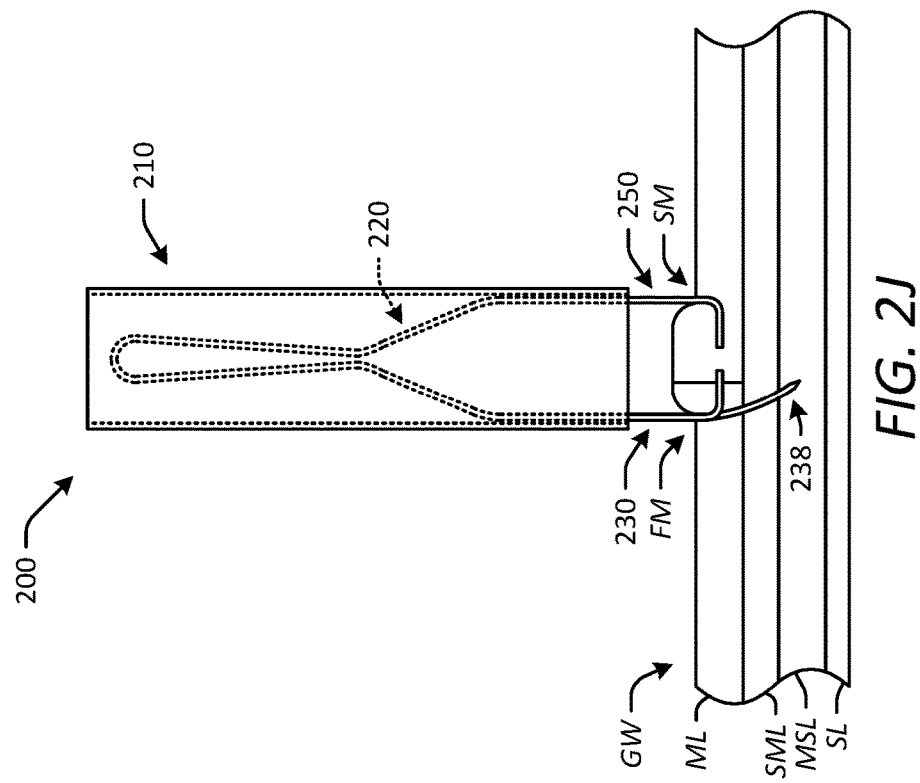
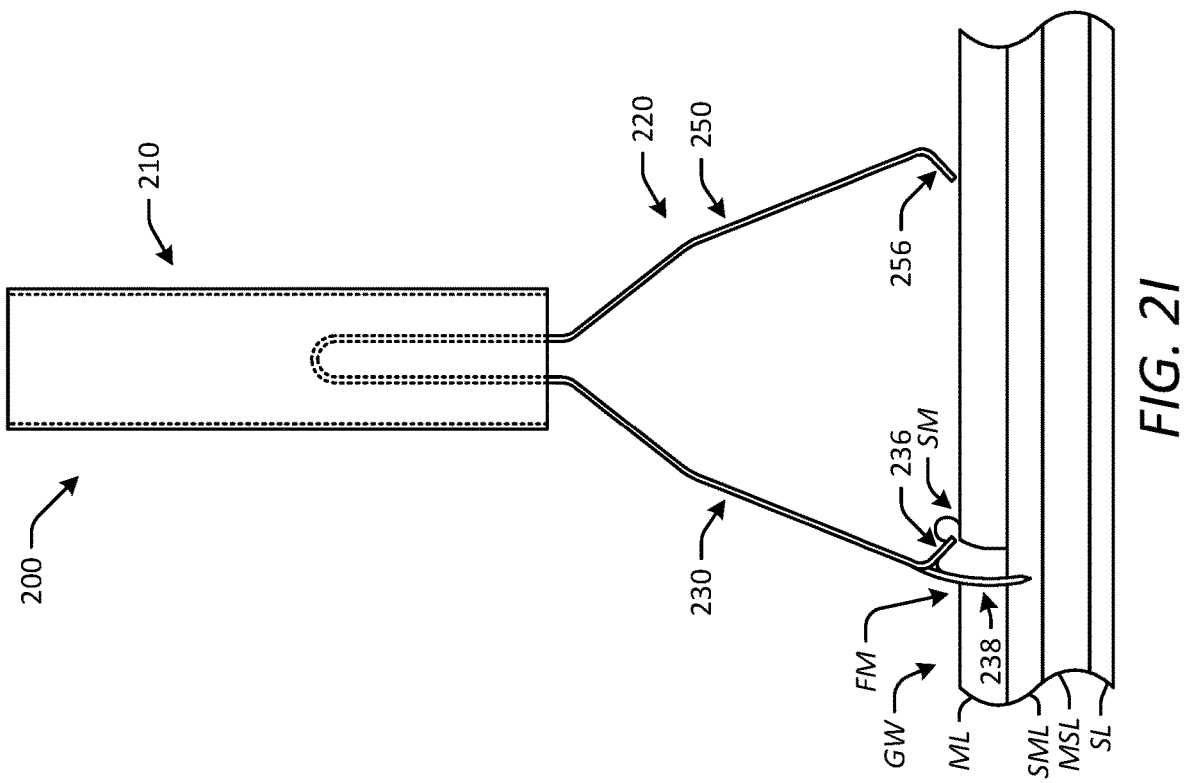

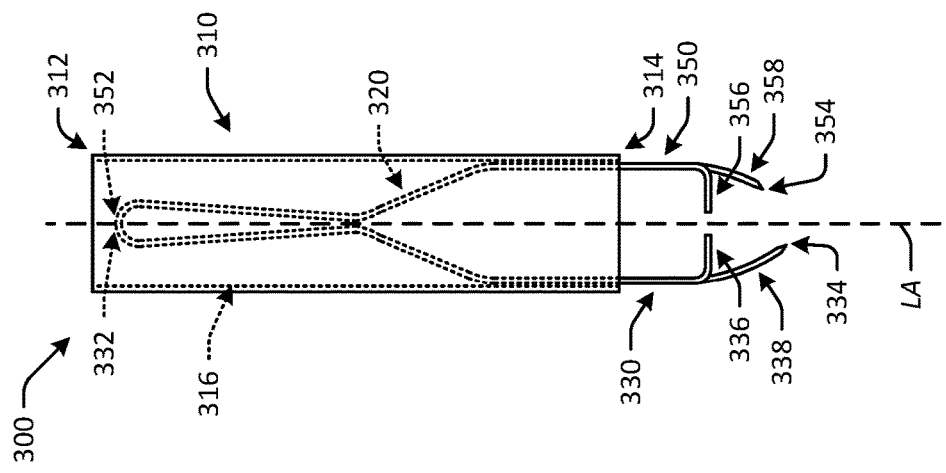
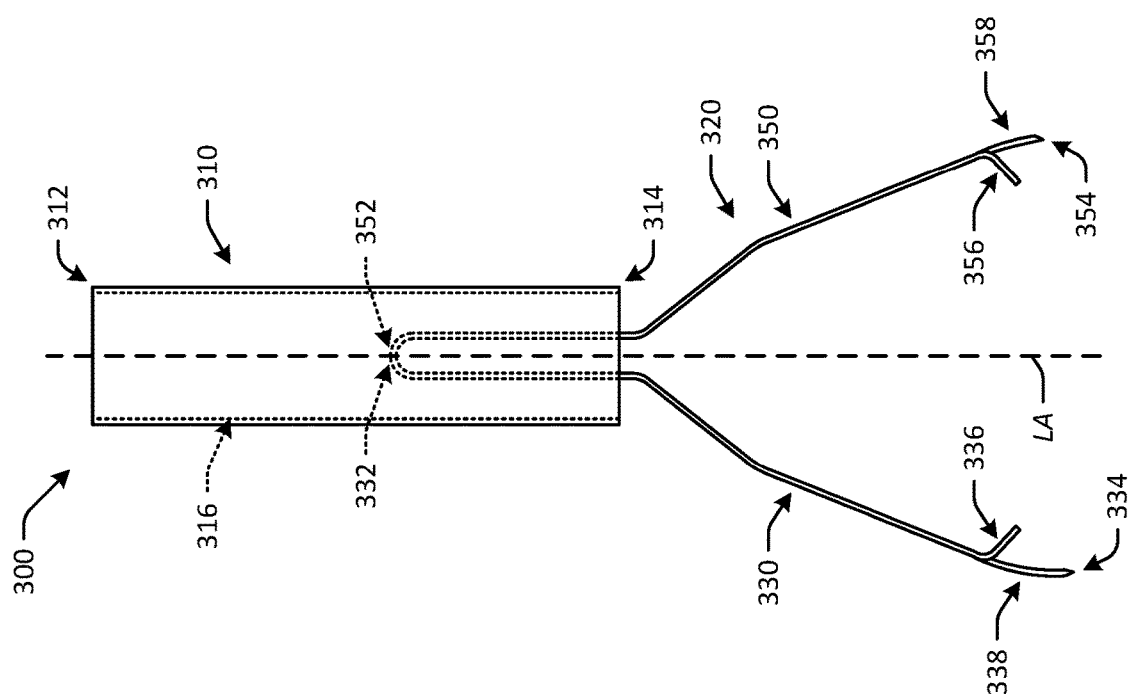
FIG. 3B
FIG. 3A

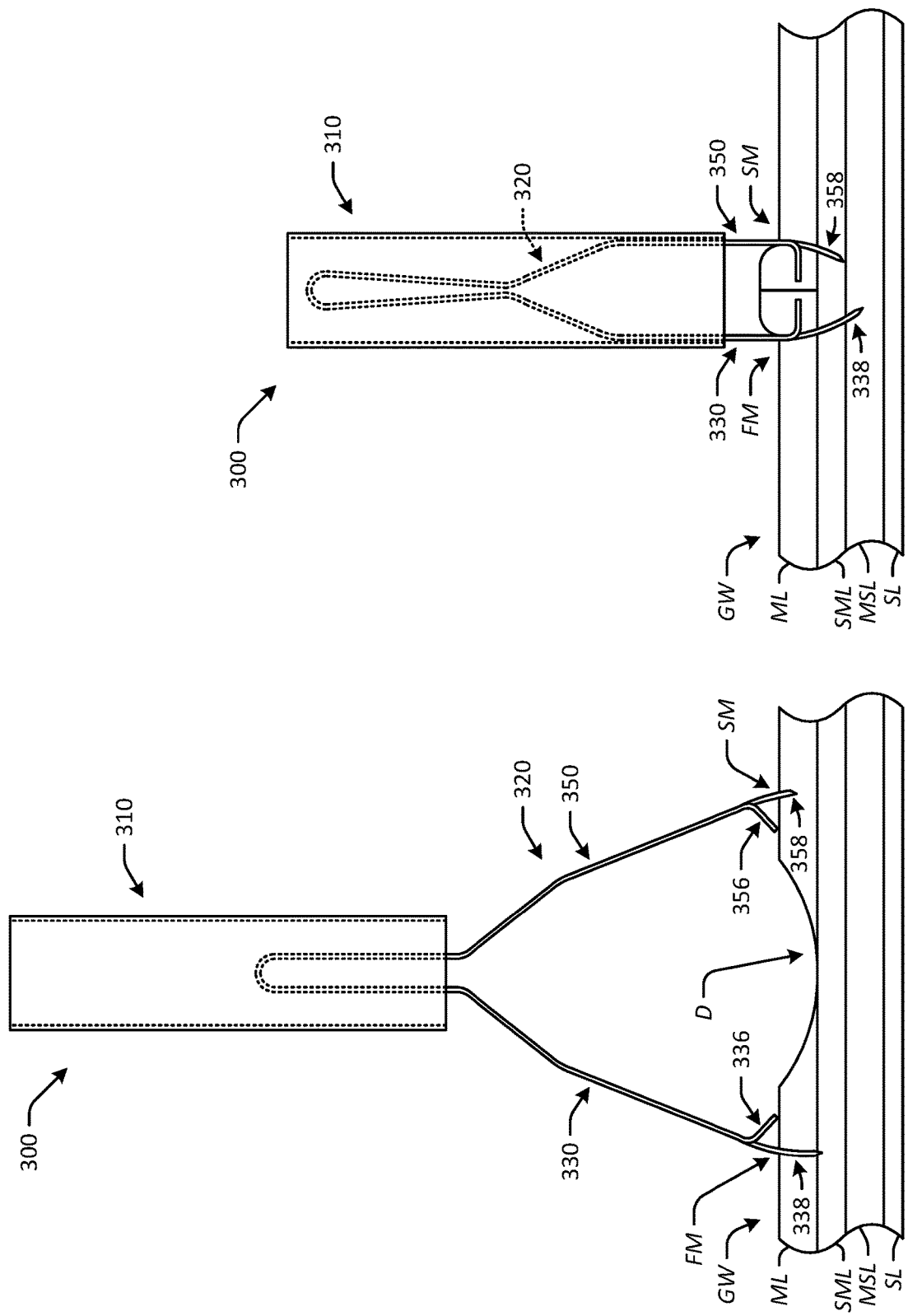

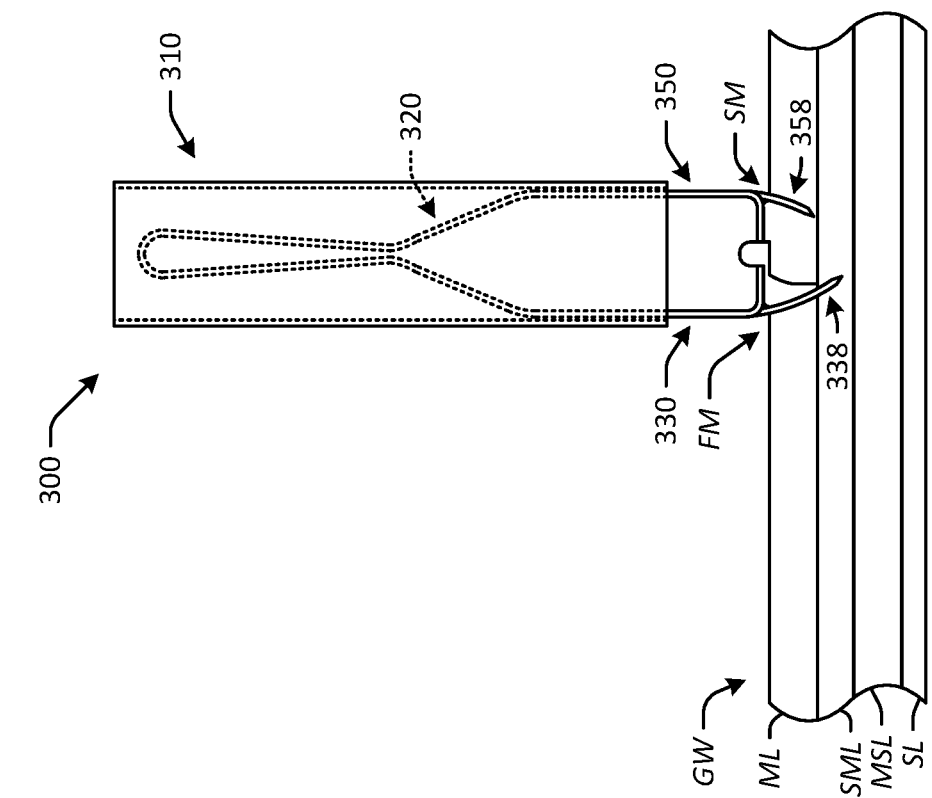
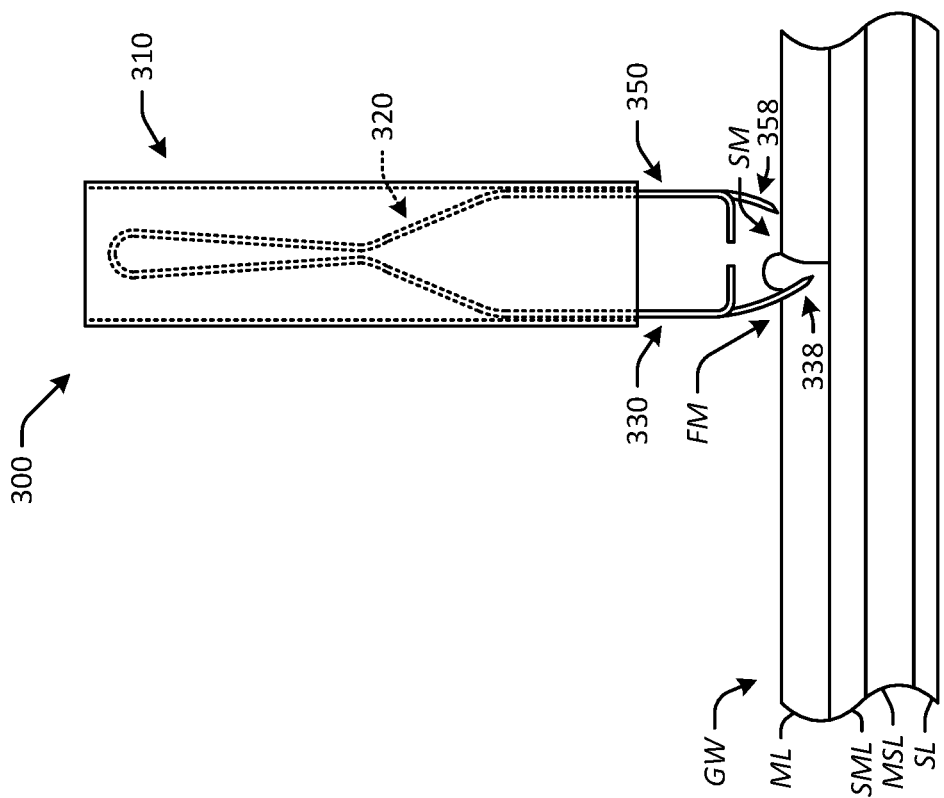

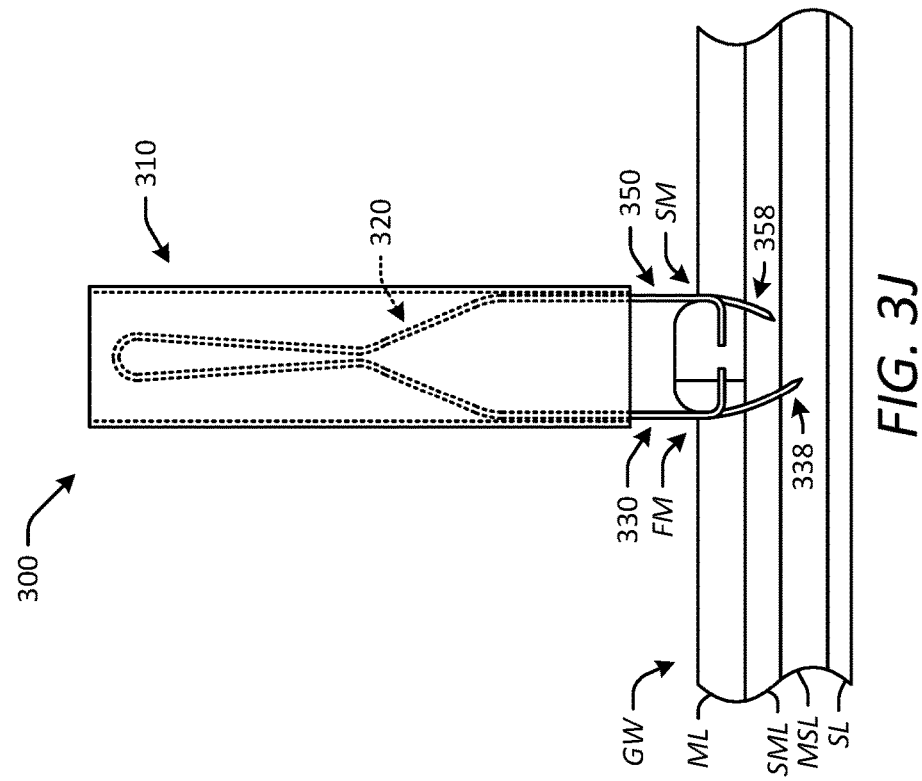
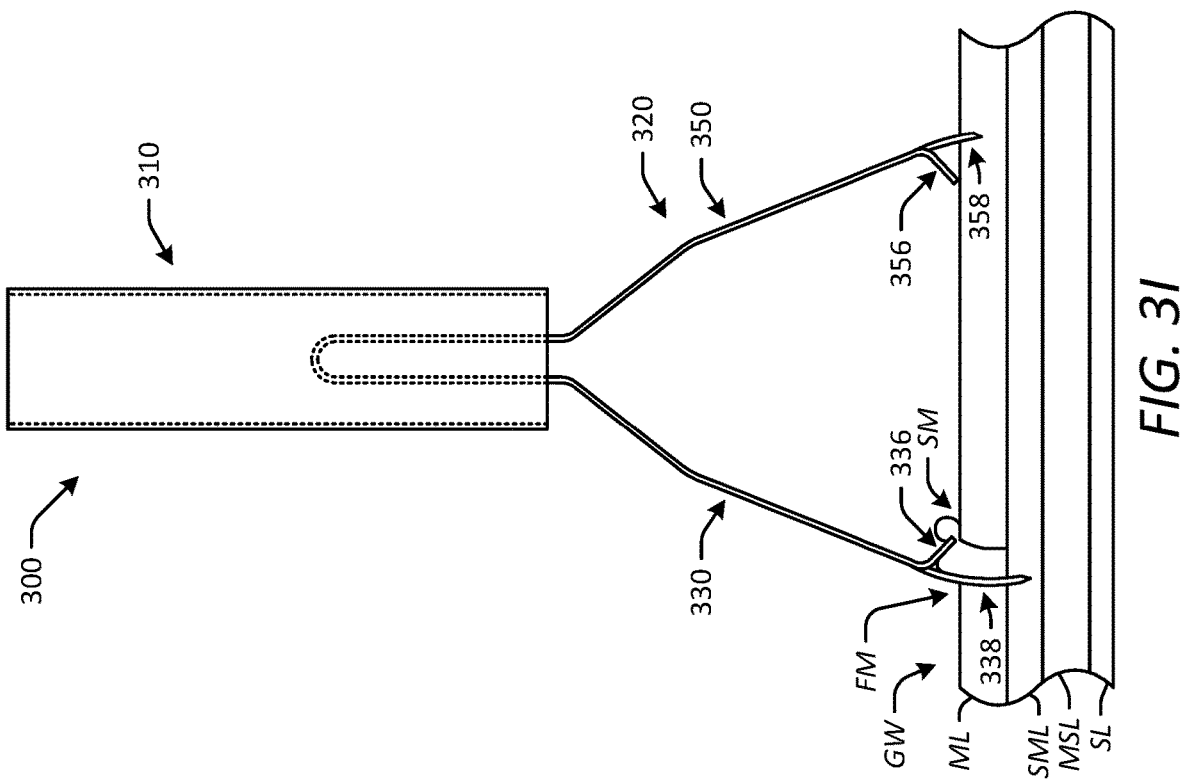
FIG. 3I
FIG. 3J

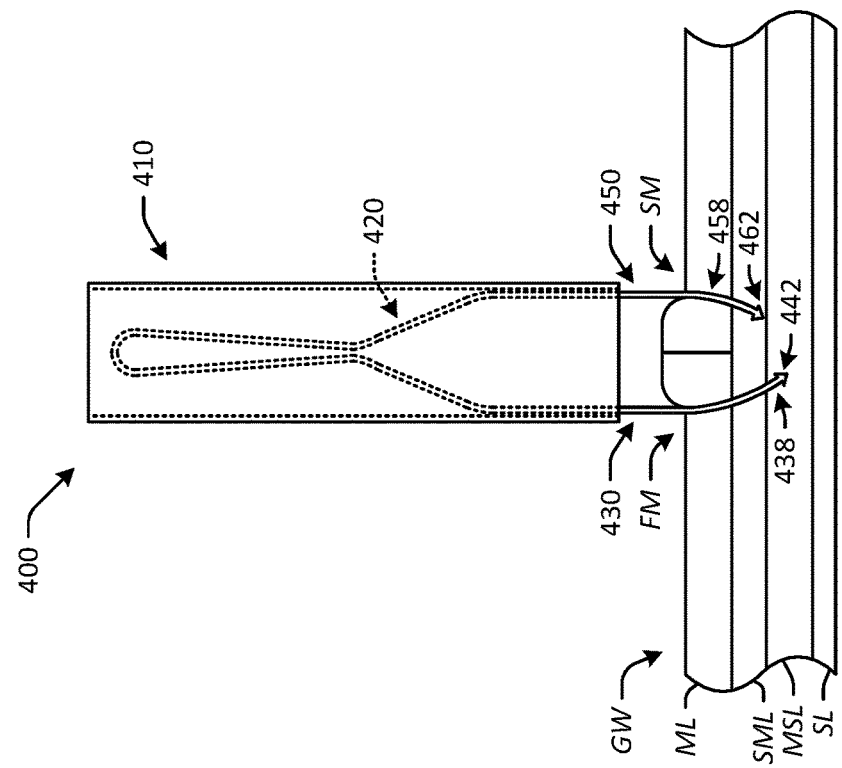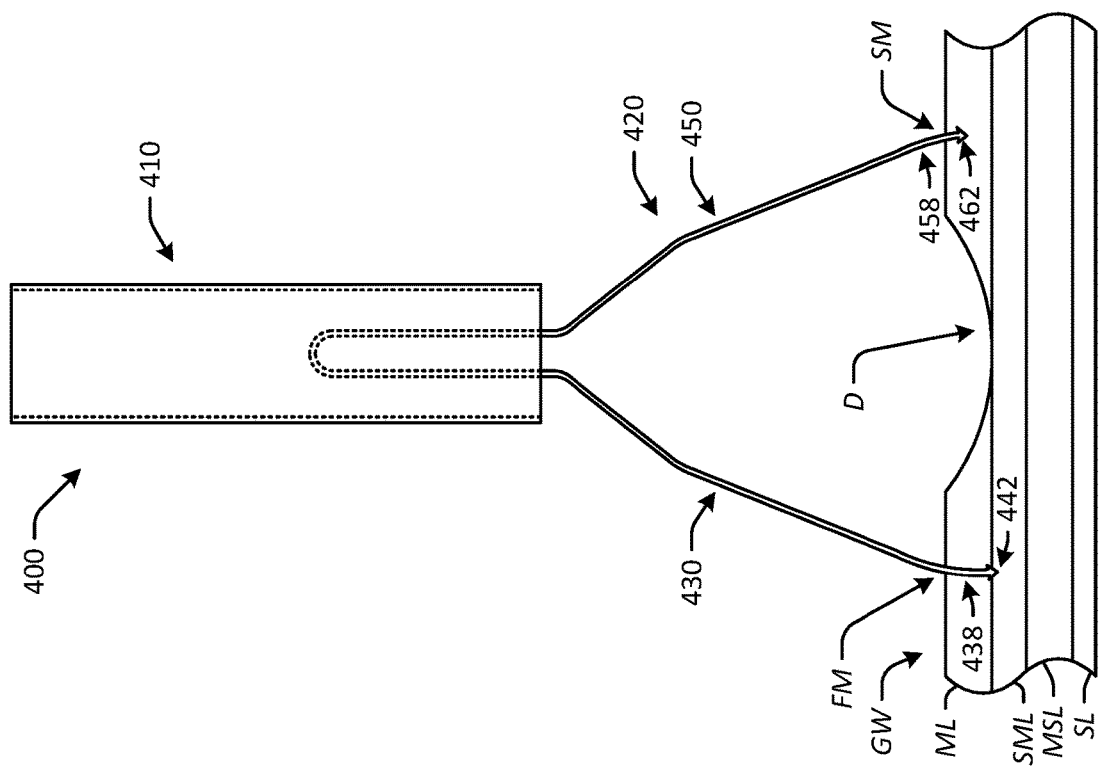

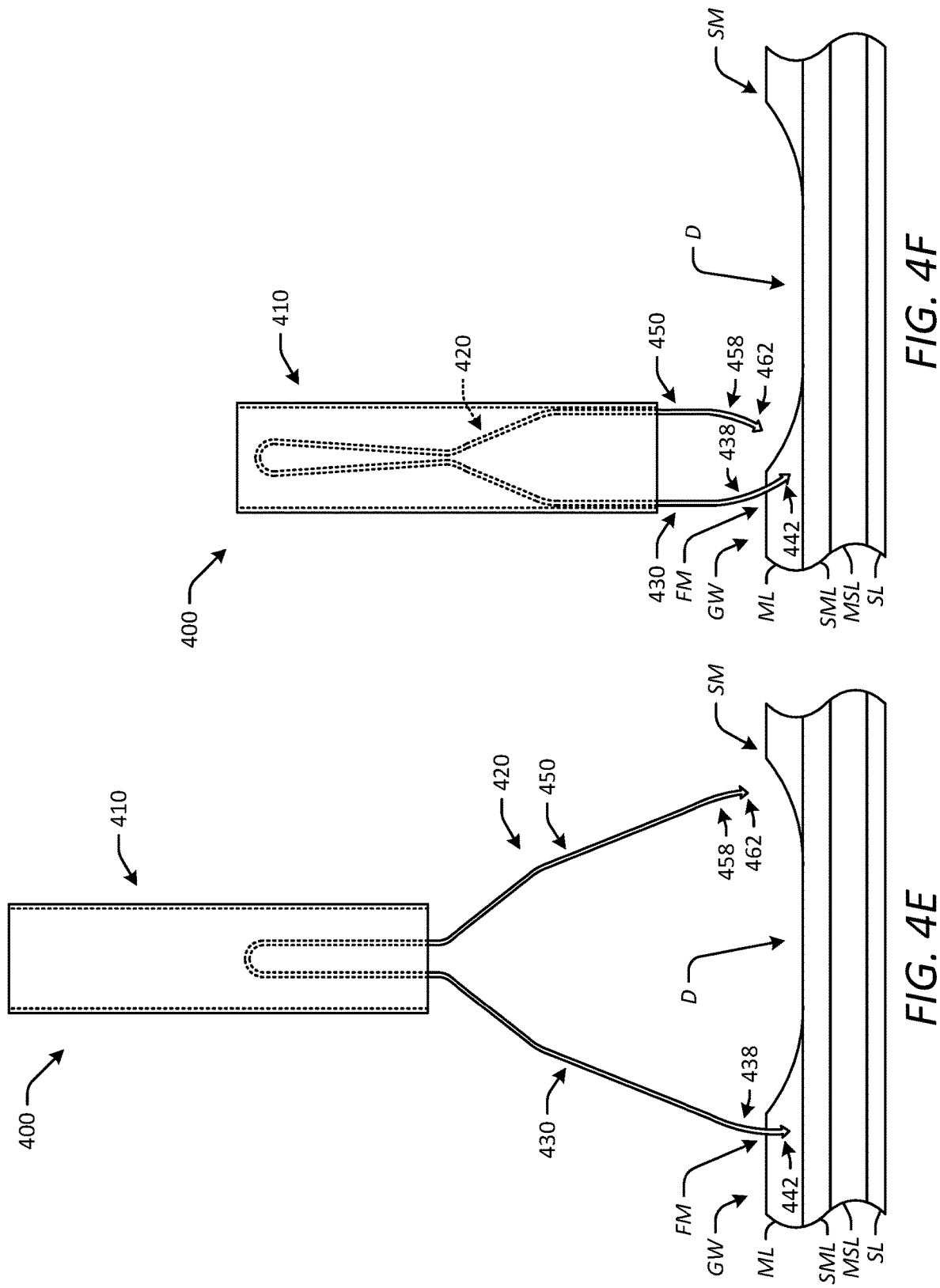

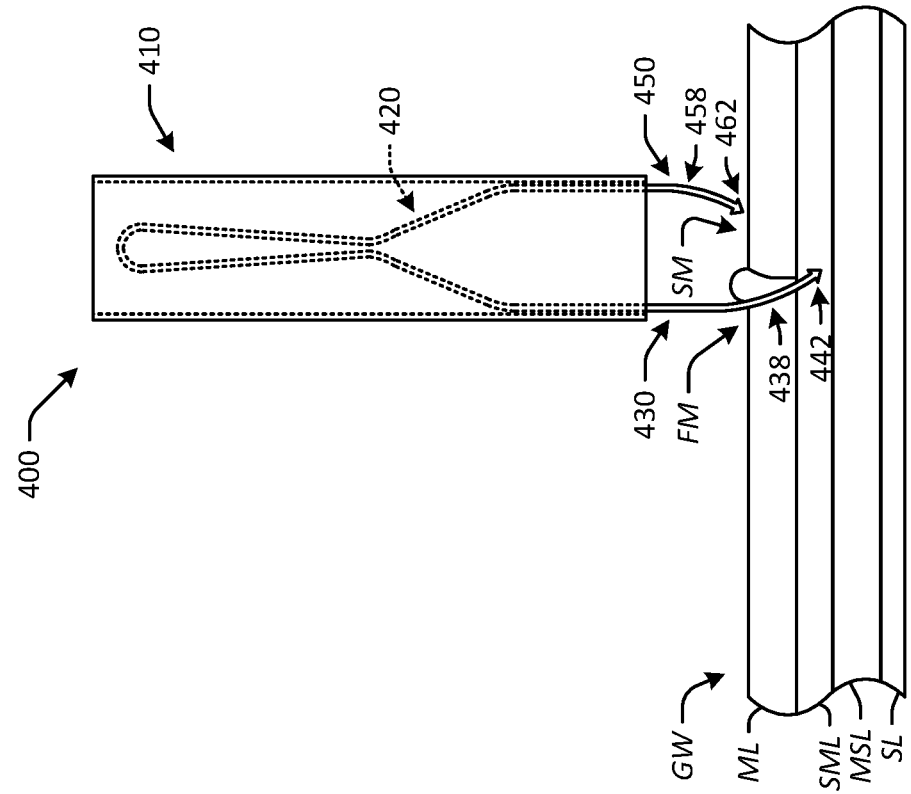
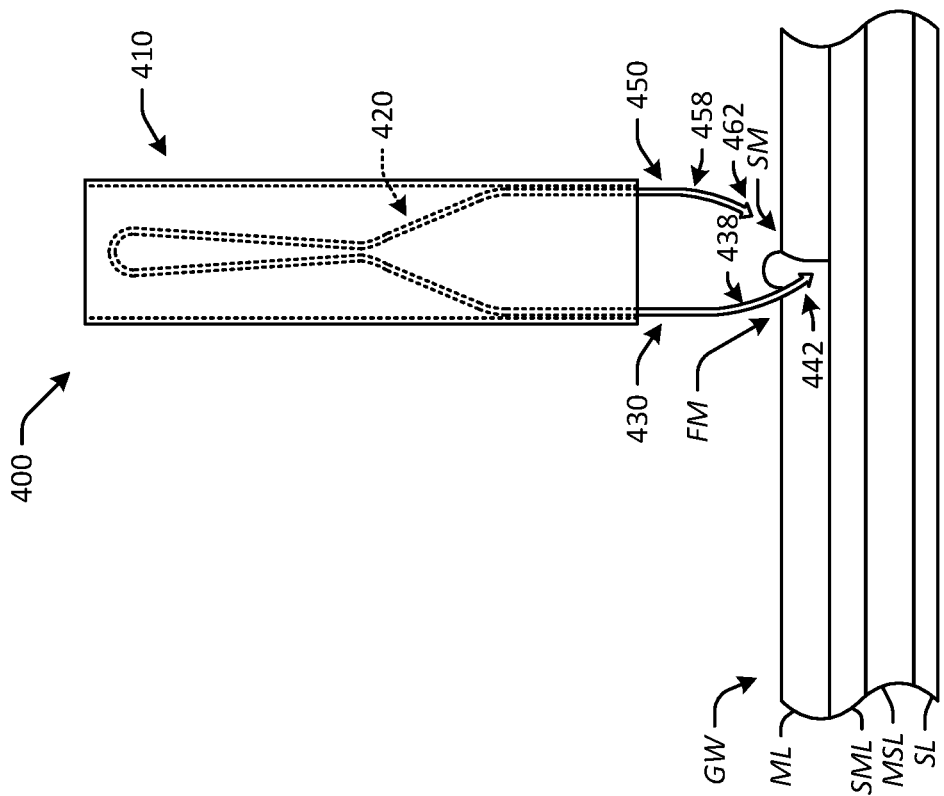

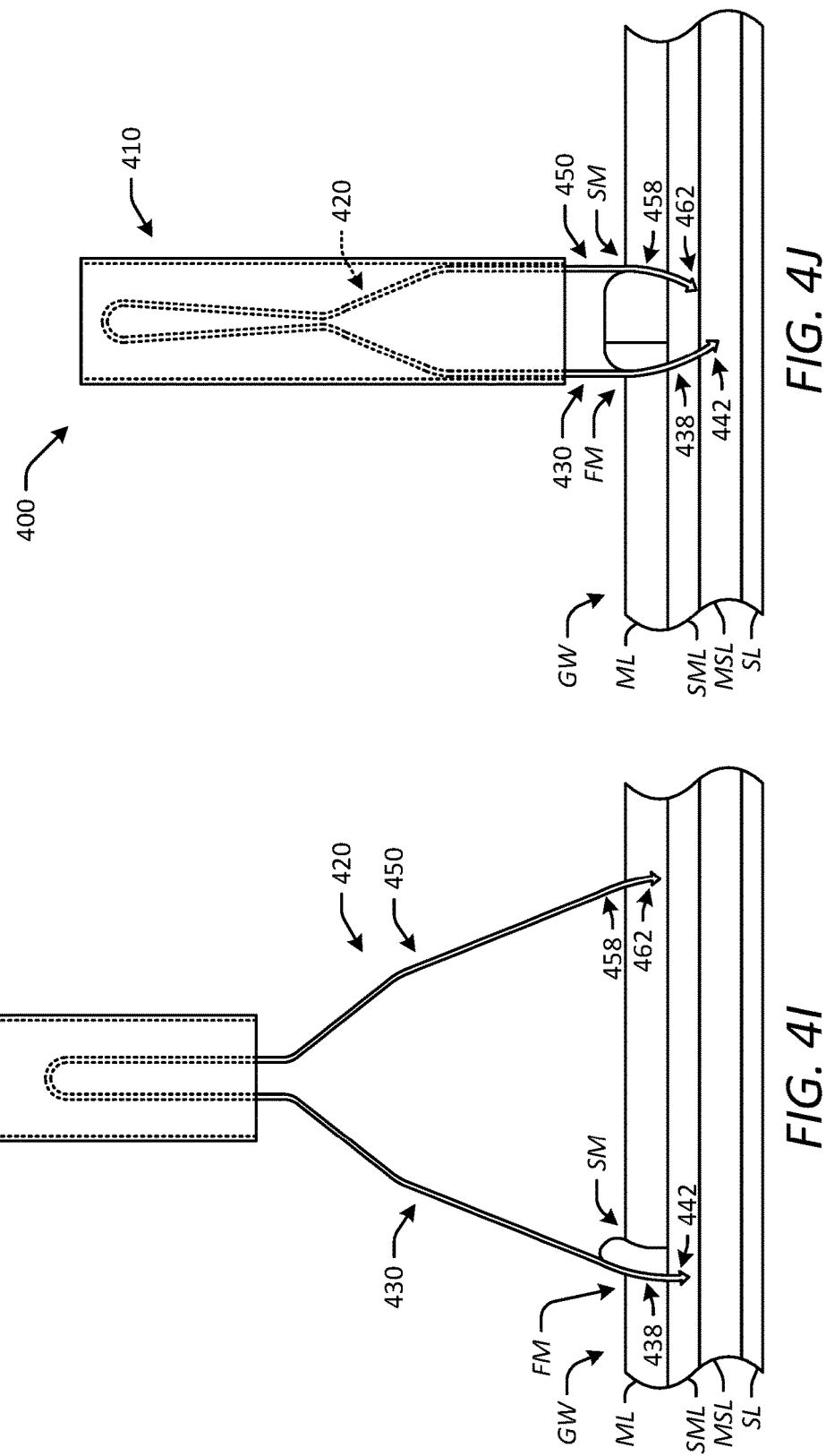

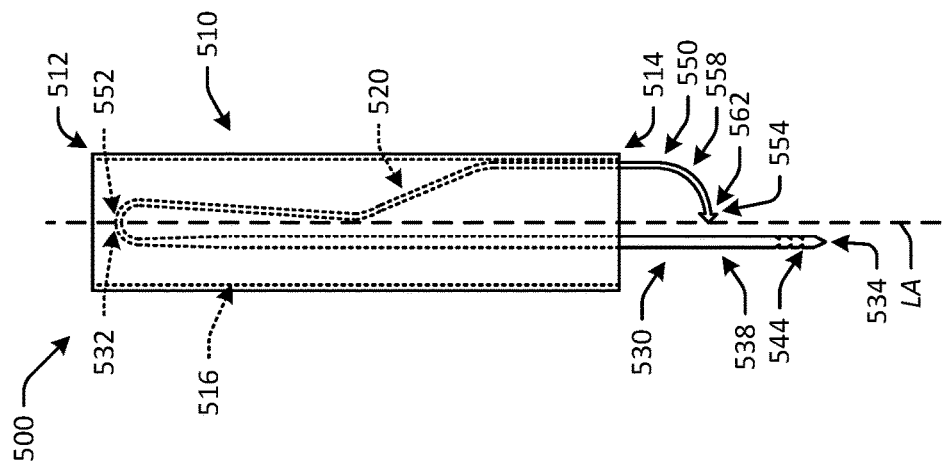
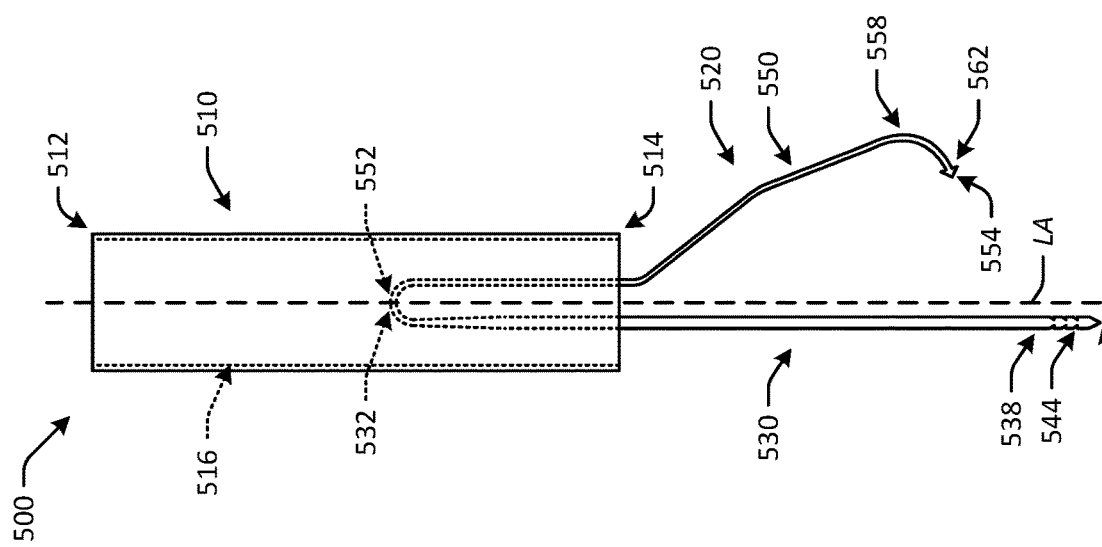

ENDOSCOPIC CLIP DEVICES AND RELATED METHODS FOR MUCOSAL DEFECT AND TRANSMURAL PERFORATION CLOSURE

CROSS-REFERENCE TO RELATED APPLICATIONS

This application claims priority to and the benefit of U.S. Provisional Patent Application No. 63/258,814, filed on Jun. 1, 2021, and entitled "Mucosal Defect and Transmural Defect Closure," which is expressly incorporated herein by reference in its entirety.

FIELD OF THE DISCLOSURE

The present disclosure relates generally to medical devices and more particularly to endoscopic clip devices and related methods for mucosal defect and transmural perforation closure.

BACKGROUND OF THE DISCLOSURE

In certain instances, endoscopic clip devices may be used for closure of a defect formed in the gastrointestinal wall of the gastrointestinal tract of a patient. For example, a mucosal defect may be formed by endoscopic submucosal dissection (ESD) performed to remove a polyp from the gastrointestinal wall. The resulting mucosal defect may be relatively large, for example, having a length of between 2 cm and 4 cm, and thus closure of the mucosal defect may be necessary or desirable to inhibit subsequent perforation of the gastrointestinal wall and promote healing of the dissected mucosal layer thereof. In some instances, ESD may result in active bleeding in the gastrointestinal wall at the treatment site, necessitating closure of the defect which may result in closure of the bleeding vessel. Various types of existing endoscopic clip devices may be used for closure of a mucosal defect, which generally may be achieved by grasping opposing resection margins along the defect and approximating the margins to close the defect.

One type of endoscopic clip device is a through-the-scope (TTS) clip device that is configured to be advanced through an operative channel of an endoscope to the treatment site. Existing TTS clip devices generally include a sleeve and a clip coupled to the sleeve and configured for moving between an open configuration and a closed configuration, for example, by moving the clip relative to the sleeve. The clip typically may include a first clip arm and a second clip arm disposed opposite one another and each having a grasping feature, such as a claw, disposed at the distal end of the respective clip arm. When the clip is in the open configuration, the distal ends of the clip arms may be spaced apart from one another by a sufficient distance to allow engagement of tissue of the gastrointestinal wall. As the clip is moved from the open configuration to the closed configuration, the distal ends of the clip arms may be drawn toward one another to grasp the engaged tissue. Generally, the first clip arm may be used to engage a first margin along a defect, and the second clip arm may be used to engage an opposing second margin along the defect. Upon engaging the margins with the respective clip arms, the clip may be moved to the closed position, thereby approximating the margins in a linear manner to facilitate closure of the defect. Multiple TTS clip devices typically may be used for closure of a defect, with the number of TTS clip devices used depending on the size of the defect. In this manner, each of the TTS clip devices used may approximate respective portions of the margins and thus provide closure of a respective portion of the defect.

Existing TTS clip devices generally are configured such that the clip arms grasp the tissue superficially, with the distal ends of the clip arms typically engaging only the mucosal layer of the gastrointestinal wall. When a TTS clip device is used for closure of a relatively small mucosal defect, the clip may be able to span a width of the defect when the clip is in the open configuration, thereby allowing the distal end of the first clip arm to engage the first margin while the distal end of the second clip arm engages the second margin. The clip then may be moved to the closed configuration to approximate the margins, grasping the engaged mucosal tissue therebetween. When a TTS clip device is used for closure of a larger mucosal defect, the clip may be unable to span a width of the defect when the clip is in the open configuration. In this scenario, with the clip in the open configuration, the distal end of the first clip arm may engage the first margin, and then the clip may be moved to the closed configuration, such that the engaged mucosal tissue is grasped between the distal ends of the clip arms. Next, the TTS clip device may be used to pull the first margin toward the second margin while the clip is in the closed configuration. The clip then may be moved to the open configuration to allow the distal end of the second clip arm to grasp the second margin and subsequently moved back to the closed configuration to approximate the margins, grasping the engaged mucosal tissue therebetween. Although this technique may be suitable in some instances, a particular problem may arise when the clip is moved to the open configuration to allow the second clip arm to engage the second margin. Specifically, due to tension applied to the first margin when the first margin is pulled toward the second margin, the mucosal tissue of the first margin may slip off of the first clip arm when the clip is moved to the open configuration. In other words, because of the applied tension, the first clip arm may be unable to effectively grip the first margin when the clip is moved to the open configuration.

Existing TTS clip devices may present additional problems when used to close a defect that extends deeper than the mucosal layer of the gastrointestinal wall. For example, when a defect extends into the submucosal layer, the muscularis layer, or the serosal layer, TTS clip devices may be unable to approximate the opposing margins of the defect along these deeper layers of the gastrointestinal wall. In particular, although a TTS clip device may be able to approximate the margins along the mucosal layer, approximation of the deeper layers may not be possible because the clip arms may grasp only the mucosal tissue of the margins. For these same reasons, existing TTS clip devices also may be unsuitable for closure of a transmural perforation in a gastrointestinal wall (i.e., a complete perforation extending through each of the mucosal, submucosal, muscularis, and serosal layers).

Another type of endoscopic clip device is an over-the-scope (OTS) clip device that is configured to be mounted on a circumferential cap positioned over a distal end portion of an endoscope and deployed therefrom. Existing OTS clip devices generally include a unitary clip having a circumferential configuration, with two sets of grasping features, such as claws, disposed opposite one another along the circumference of the clip. In this manner, the clip may resemble an animal trap, with the clip being movable from an open configuration for receiving tissue within the through opening of the clip to a closed configuration for grasping the received tissue with the grasping features of the clip. The clip generally may be biased to the closed configuration but maintained in the open configuration by the circumferential cap prior to deployment of the OTS clip device therefrom. In this manner, as the OTS clip device is deployed from the circumferential cap, the bias may cause the clip to automatically move from the open configuration to the closed configuration, grasping the received tissue. Suction may be applied to the tissue through the endoscope, causing the tissue to be drawn into the circumferential cap prior to deploying the OTS clip device, such that the tissue is received within the through opening of the clip prior to the clip moving to the closed configuration.

In some instances, a single OTS clip device may be used for closure of a defect, with the clip surrounding the defect and approximating the margins of the defect in a circumferential manner. In other instances, multiple OTS clip devices may be used for closure of a defect, such as when the defect is larger than the circumference of the clip or when a first OTS clip device is not positioned properly to surround and close the entire defect. According to different applications, OTS clip devices may be used for closure of a mucosal defect or a defect that extends into the submucosal layer, the muscularis layer, or the serosal layer of the gastrointestinal wall. Depending on how the OTS clip device is positioned and how much tissue is drawn into and engaged by the clip, in some instances, the clip may be able to approximate the margins of the defect along each of the resected layers of the gastrointestinal wall. In some instances, OTS clip devices also may be used for closure of a transmural perforation in a gastrointestinal wall. As compared to TTS clip devices, OTS clip devices may present certain problems that make their use less desirable for closure of a defect or a transmural perforation. First, use of OTS clip devices may be considered more aggressive than TTS clip devices, with OTS clip devices presenting a higher risk of inadvertently engaging and damaging a vital tissue or organ. Second, because the clip of OTS clip devices is biased to automatically move from the open configuration to the closed configuration upon deployment from the circumferential cap, the clip does not allow for fine tuning in engaging the tissue. Third, because OTS clip devices are irreversible (i.e., the clip can be moved from the open configuration to the closed configuration only once and cannot be reopened), they do not allow for repositioning of the clip in the event that the clip is improperly placed relative to a defect. Finally, due to their irreversible nature, OTS clip devices are not easily removable, typically requiring that the device be fragmented in order to achieve removal.

A need therefore exists for improved endoscopic clip devices and related methods for closure of a mucosal defect or a transmural perforation in a gastrointestinal wall, which may overcome one or more of the above-mentioned challenges associated with existing endoscopic clip devices and closure techniques.

SUMMARY OF THE DISCLOSURE

The present disclosure provides endoscopic clip devices and related methods of using such endoscopic clip devices for closure of a mucosal defect or a transmural perforation in a gastrointestinal wall.

In one aspect, an endoscopic clip device for closure of a mucosal defect or a transmural perforation in a gastrointestinal wall is provided. In one embodiment, the endoscopic clip device may include a sleeve and a clip disposed at least partially within and coupled to the sleeve. The clip may be configured for reversibly moving between an open configuration for positioning relative to the gastrointestinal wall and a closed configuration for closing the mucosal defect or the transmural perforation. The clip may include a first clip arm configured for engaging the mucosal layer and the submucosal layer of the gastrointestinal wall and including a first needle extending to a distal end of the first clip arm and configured for advancing through the mucosal layer and into at least the submucosal layer of the gastrointestinal wall, and a second clip arm disposed opposite the first clip arm and configured for engaging the mucosal layer of the gastrointestinal wall. The endoscopic clip device may be configured for advancing through an operative channel of an endoscope or an overtube having a tortuous shape.

In some embodiments, the clip may be asymmetric such that the first clip arm and the second clip arm are not mirror images of one another. In some embodiments, the first clip arm may have a first length extending from a proximal end of the first clip arm to the distal end of the first clip arm, the second clip arm may have a second length extending from a proximal end of the second clip arm to a distal end of the second clip arm, and the first length may be different from the second length. In some embodiments, the first clip arm also may include a first claw spaced apart from the distal end of the first clip arm and extending transverse to the first needle, and the first claw may be configured for engaging the mucosal layer of the gastrointestinal wall when the first needle extends through the mucosal layer and into at least the submucosal layer of the gastrointestinal wall. In some embodiments, the second clip arm may include a second claw configured for engaging the mucosal layer of the gastrointestinal wall. In some embodiments, the second claw may be disposed at a distal end of the second clip arm. In some embodiments, the second clip arm also may include a second needle extending to a distal end of the second clip arm and configured for advancing through the mucosal layer and into at least the submucosal layer of the gastrointestinal wall, the second claw may be spaced apart from the distal end of the second clip arm and extend transverse to the second needle, and the second claw may be configured for engaging the mucosal layer of the gastrointestinal wall when the second needle extends through the mucosal layer and into at least the submucosal layer of the gastrointestinal wall.

In some embodiments, the second clip arm may include a second needle extending to a distal end of the second clip arm and configured for advancing into at least the mucosal layer of the gastrointestinal wall. In some embodiments, the first clip arm may have a first length extending from a proximal end of the first clip arm to the distal end of the first clip arm, the second clip arm may have a second length extending from a proximal end of the second clip arm to a distal end of the second clip arm, and the first length may be different from the second length. In some embodiments, the first needle may have a curved shape, and the second needle may have a curved shape. In some embodiments, the first needle may have a straight shape extending parallel to or coaxial with a longitudinal axis of the sleeve and configured for extending parallel to or coaxial with a longitudinal axis of the operative channel, and the second needle may have a curved shape. In some embodiments, the first needle may include a first arrowhead tip disposed at the distal end of the first clip arm, and the second needle may include a second arrowhead tip disposed at the distal end of the second clip arm. In some embodiments, the first needle may include a plurality of barbs spaced apart from the distal end of the first clip arm. In some embodiments, the first needle may include a plurality of serrations spaced apart from the distal end of the first clip arm. In some embodiments, the second needle may be configured for advancing through the mucosal layer and into at least the submucosal layer of the gastrointestinal wall.

In another aspect, a method of using an endoscopic clip device for closure of a mucosal defect or a transmural perforation in a gastrointestinal wall is provided. In one embodiment, the method may include advancing the endoscopic clip device through an operative channel of an endoscope or an overtube having a tortuous shape. The endoscopic clip device may include a sleeve and a clip disposed at least partially within and coupled to the sleeve. The clip may be configured for reversibly moving between an open configuration and a closed configuration. The clip may include a first clip arm including a first needle extending to a distal end of the first clip arm, and a second clip arm disposed opposite the first clip arm. The method also may include positioning the clip relative to the gastrointestinal wall while the clip is in the open configuration, engaging a first margin along the mucosal defect or the transmural perforation with the first clip arm by advancing the first needle into at least the mucosal layer of the gastrointestinal wall, pulling the first margin toward a second margin along the mucosal defect or the transmural perforation, advancing the first needle into at least the submucosal layer of the gastrointestinal wall, engaging the second margin with the second clip arm by engaging the mucosal layer of the gastrointestinal wall, and moving the clip from the open configuration to the closed configuration such that the first margin and the second margin are approximated in a linear manner.

In some embodiments, the method also may include, after engaging the first margin with the first clip arm by advancing the first needle into at least the mucosal layer of the gastrointestinal wall, moving the clip from the open configuration to the closed configuration. In some embodiments, pulling the first margin toward the second margin may include pulling the first margin toward the second margin while the clip is in the closed configuration, and advancing the first needle into at least the submucosal layer of the gastrointestinal wall may include advancing the first needle into at least the submucosal layer of the gastrointestinal wall while the clip is in the closed configuration. In some embodiments, advancing the first needle into at least the submucosal layer of the gastrointestinal wall may include advancing the first needle into at least the submucosal layer of the gastrointestinal wall near the second margin. In some embodiments, the method also may include, after advancing the first needle into at least the submucosal layer of the gastrointestinal wall, moving the clip from the closed configuration to the open configuration. In some embodiments, engaging the second margin with the second clip arm may include engaging the second margin with the second clip arm while the clip is in the open configuration. In some embodiments, the second clip arm may include a second needle extending to a distal end of the second clip arm, and engaging the second margin with the second clip arm may include advancing the second needle into at least the mucosal layer of the gastrointestinal wall.

These and other aspects and improvements of the present disclosure will become apparent to one of ordinary skill in the art upon review of the following detailed description when taken in conjunction with the several drawings and the appended claims.

BRIEF DESCRIPTION OF THE DRAWINGS

FIGS. 2C and 2D are side views of the endoscopic clip device of FIG. 2A, illustrating an example method for closure of a mucosal defect in a gastrointestinal wall in accordance with embodiments of the disclosure. FIGS. 2E-2J are side views of the endoscopic clip device of FIG. 2A, illustrating another example method for closure of a mucosal defect in a gastrointestinal wall in accordance with embodiments of the disclosure.

FIG. 3A is a side view of an example endoscopic clip device in accordance with embodiments of the disclosure, showing a sleeve and a clip of the endoscopic clip device, with the clip in an open configuration. FIG. 3B is a side view of the endoscopic clip device of FIG. 3A, showing the clip in a closed configuration. FIGS. 3C and 3D are side views of the endoscopic clip device of FIG. 3A, illustrating an example method for closure of a mucosal defect in a gastrointestinal wall in accordance with embodiments of the disclosure. FIGS. 3E-3J are side views of the endoscopic clip device of FIG. 3A, illustrating another example method for closure of a mucosal defect in a gastrointestinal wall in accordance with embodiments of the disclosure.

FIGS. 4C and 4D are side views of the endoscopic clip device of FIG. 4A, illustrating an example method for closure of a mucosal defect in a gastrointestinal wall in accordance with embodiments of the disclosure. FIGS. 4E-4J are side views of the endoscopic clip device of FIG. 4A, illustrating another example method for closure of a mucosal defect in a gastrointestinal wall in accordance with embodiments of the disclosure.

FIG. 5A is a side view of an example endoscopic clip device in accordance with embodiments of the disclosure, showing a sleeve and a clip of the endoscopic clip device, with the clip in an open configuration. FIG. 5B is a side view of the endoscopic clip device of FIG. 5A, showing the clip in a closed configuration.

Figure 1B:
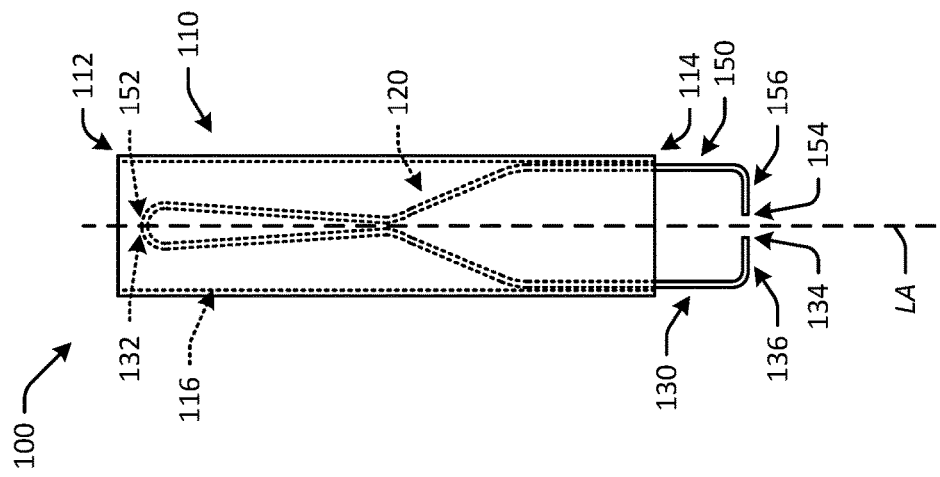
FIG. 1B is a side view of the endoscopic clip device of FIG. 1A, showing the clip in a closed configuration.

The detailed description is set forth with reference to the accompanying drawings. The drawings are provided for purposes of illustration only and merely depict example embodiments of the disclosure. The drawings are provided to facilitate understanding of the disclosure and shall not be deemed to limit the breadth, scope, or applicability of the disclosure. The use of the same reference numerals indicates similar, but not necessarily the same or identical components. Different reference numerals may be used to identify similar components. Various embodiments may utilize elements or components other than those illustrated in the drawings, and some elements and/or components may not be present in various embodiments. The use of singular terminology to describe a component or element may, depending on the context, encompass a plural number of such components or elements and vice versa.

DETAILED DESCRIPTION OF THE DISCLOSURE

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional. In some instances, well known methods, procedures, and components have not been described in detail so as not to unnecessarily obscure aspects of the embodiments.

The present disclosure provides improved endoscopic clip devices and related methods for closure of a mucosal defect or a transmural perforation in a gastrointestinal wall, which may overcome one or more of the above-mentioned challenges associated with existing endoscopic clip devices and closure techniques. Various benefits and advantages of the endoscopic clip devices and related methods provided herein over existing devices and techniques will be appreciated by those of ordinary skill in the art from the following description and the appended drawings.

Example Drill Guides and Methods

Figure 1A:
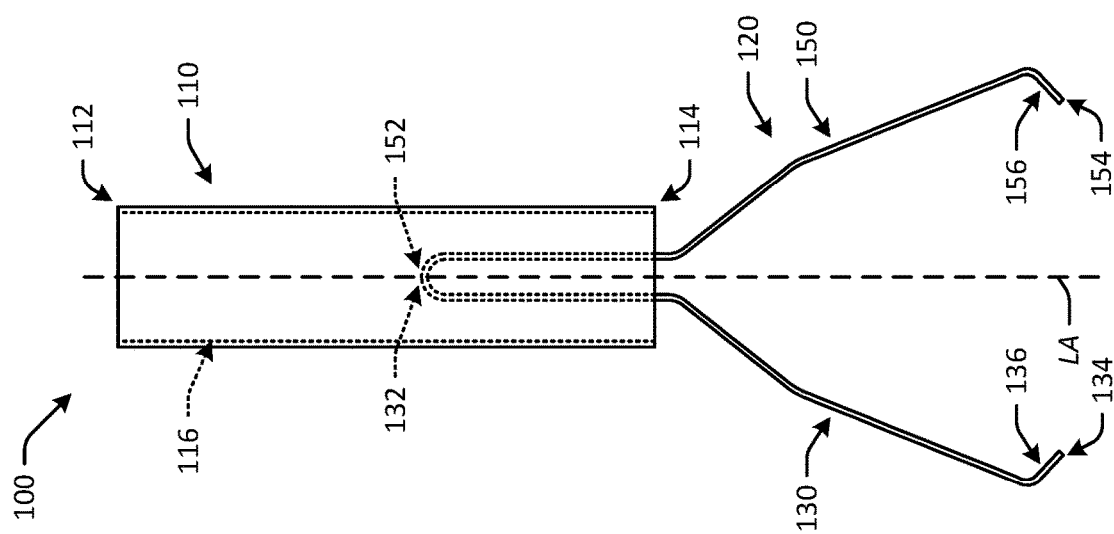
FIG. 1A is a side view of an example endoscopic clip device, showing a sleeve and a clip of the endoscopic clip device, with the clip in an open configuration.
Figure 1D:
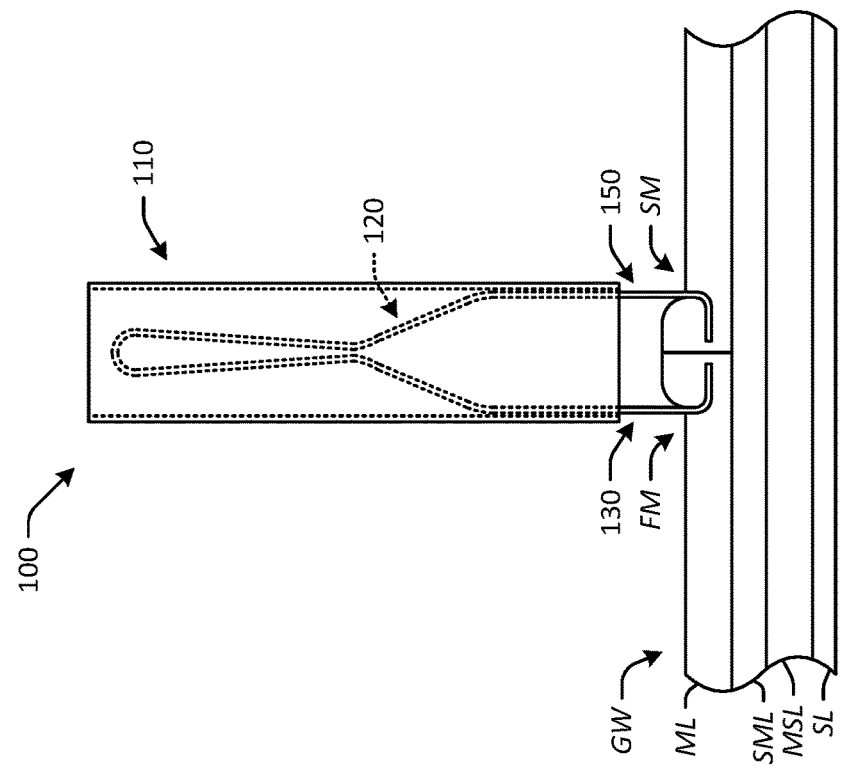
FIGS. 1C and 1D are side views of the endoscopic clip device of FIG. 1A, illustrating an example method for closure of a mucosal defect in a gastrointestinal wall.
Figure 1C:
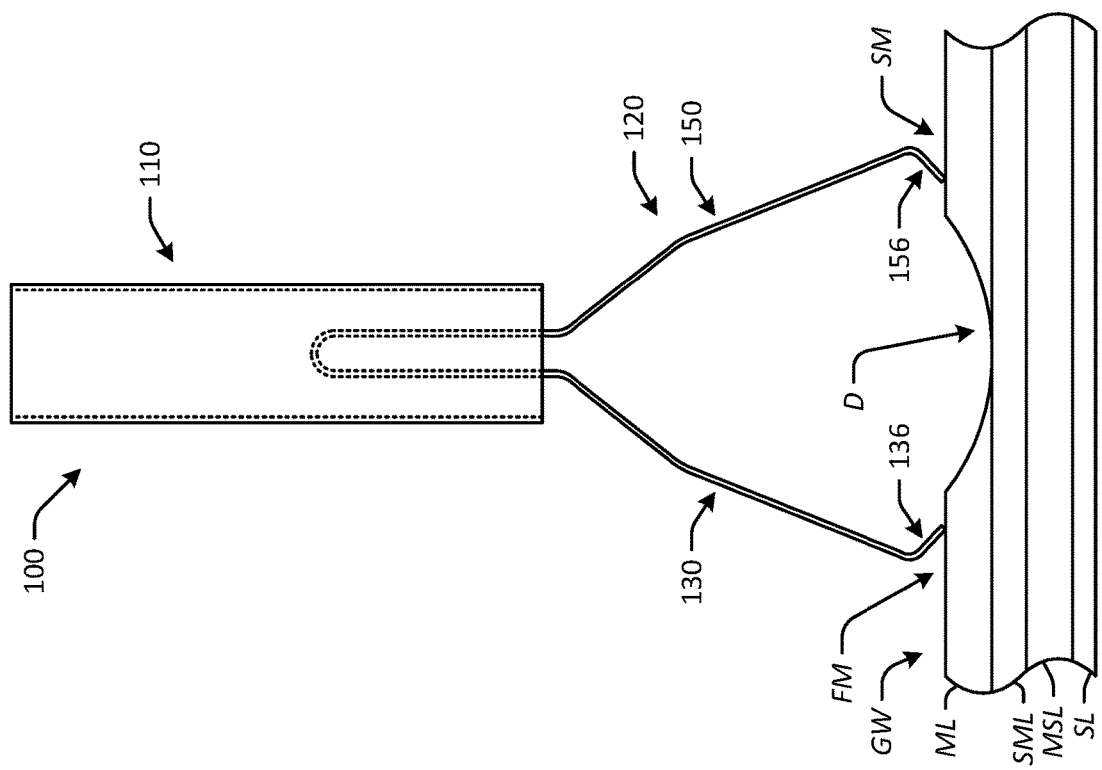

Referring now to the drawings, FIGS. 1A and 1B illustrate an example endoscopic clip device 100 (which also may be referred to as a "endoscopic device" or simply a "device") that generally resembles an existing through-the-scope (TTS) clip device. In this manner, the endoscopic clip device 100 may be configured to be advanced through an operative channel of an endoscope to a treatment site for closure of a defect, such as a mucosal defect, in a gastrointestinal wall of a patient. FIGS. 1C and 1D show the endoscopic clip device 100 being used for closure of a defect D in a gastrointestinal wall GW, as discussed further below.

According to the example of FIGS. 1A-1D, the endoscopic clip device 100 generally may include a sleeve 110 (which also may be referred to as a "shell" or a "capsule") and a clip 120 (which also may be referred to as an "endoscopic clip"). It will be appreciated that the device 100 also may include additional components other than the sleeve 110 and the clip 120, such as components that guide, control, or inhibit movement of the clip 120 relative to the sleeve 110 and/or components that facilitate interaction between the clip 120 or the sleeve 110 and mating components or features of a delivery device used to advance the device 100 through an operative channel of an endoscope and subsequently deploy the device 100 within a patient's gastrointestinal tract. For simplicity of illustration, only the sleeve 110 and the clip 120 are shown in FIGS. 1A-1D.

As shown in FIGS. 1A and 1B, the sleeve 110 may be formed as an elongated structure having a proximal end 112 and a distal end 114 disposed opposite one another along a longitudinal axis LA of the device 100. The longitudinal axis of the sleeve 110 may be coaxial with the longitudinal axis LA of the device 100. As shown, the sleeve 110 may define a passage 116 therein. In some instances, the passage 116 may extend from the proximal end 112 to the distal end 114 of the sleeve 110.

The clip 120 may be disposed at least partially within the sleeve 110 and may be coupled to the sleeve 110. As shown, a proximal portion of the clip 120 may be disposed within the passage 116 of the sleeve 110. Various components and mechanisms may be used for coupling the clip 120 to the sleeve. As shown, the clip 120 may be configured for moving relative to the sleeve 110 between different configurations. According to the illustrated example, the clip 120 may be configured for reversibly moving relative to the sleeve 110 between an open configuration, as shown in FIG. 1A, and a closed configuration, as shown in FIG. 1B. The closed configuration of the clip 120 may be used for advancing the device 100 through an operative channel of an endoscope to a treatment site and also for closing a defect in a gastrointestinal wall. The open configuration of the clip 120 may be used for positioning the device 100 relative to the gastrointestinal wall and for engaging tissue of the gastrointestinal wall with features of the clip 120 prior to closing the defect. As shown, the clip 120 may be reversibly moved between the open configuration and the closed configuration by translating the sleeve 110 relative to the clip 120 or translating the clip 120 relative to the sleeve 110 in the direction of the longitudinal axis LA of the device 100.

As shown in FIGS. 1A and 1B, the clip 120 generally may include a first clip arm 130 and a second clip arm 150 disposed opposite one another. In some instances, as shown, the clip 120 may be centered on the longitudinal axis LA of the device 100. In some instances, as shown, the clip 120 may be symmetric such that the first clip arm 130 and the second clip arm 150 are mirror images of one another. As shown, the clip 120 may be symmetric about a plane extending through the longitudinal axis LA of the device 100 and perpendicular to the views of FIGS. 1A and 1B. The first clip arm 130 may be formed as an elongated structure having a proximal end 132 and a distal end 134 disposed opposite one another in the direction of the longitudinal axis LA of the device 100. In a similar manner, the second clip arm 150 may be formed as an elongated structure having a proximal end 152 and a distal end 154 disposed opposite one another in the direction of the longitudinal axis LA of the device 100. In some instances, as shown, the proximal end 132 of the first clip arm 130 may be coupled to the proximal end 152 of the second clip arm 150. In some instances, as shown, the first clip arm 130 and the second clip arm 150 may be integrally formed with one another, with the proximal end 132 of the first clip arm 130 being directly coupled to the proximal end 152 of the second clip arm 150. In other instances, the first clip arm 130 and the second clip arm 150 may be coupled to one another by one or more additional portions or components of the clip 120 which are separately formed and attached to the clip arms 130, 150. Various arrangements of the clip arms 130, 150 and the overall clip 120 may be used.

As shown, the proximal ends 132, 152 of the clip arms 130, 150 may be disposed within the passage 116 of the sleeve 110 when the clip 120 is in the open configuration and when the clip 120 is in the closed configuration. In contrast, the distal ends 134, 154 of the clip arms 130, 150 may be disposed outside of the passage 116 of the sleeve 110 when the clip 120 is in the open configuration and when the clip 120 is in the closed configuration. As shown, the distal ends 134, 154 of the clip arms 130, 150 may move toward one another when the clip 120 is moved from the open configuration to the closed configuration, and the distal ends 134, 154 of the clip arms 130, 150 may move away from one another when the clip 120 is moved from the closed configuration to the open configuration. Various contours or profiles of the clip arms 130, 150, as shown in the views of FIGS. 1A and 1B, may be used. The contours or profiles of the clip arms 130, 150 may dictate how the clip arms 130, 150 move relative to each other and the sleeve 110 when the clip 120 is moved between the open configuration and the closed configuration. In some instances, the clip arms 130, 150 may engage one or more features of the sleeve 110 when the clip 120 is moved from the open configuration to the closed configuration and/or when the clip 120 is moved from the closed configuration to the open configuration, with the contours or profiles of the clip arms 130, 150 and/or the engaged features guiding movement of the clip arms 130, 150 relative to each other and the sleeve 110. In some instances, the clip arms 130, 150 additionally or alternatively may engage one or more features of other components of the device 100 (i.e., other than the sleeve 110) when the clip 120 is moved from the open configuration to the closed configuration and/or when the clip 120 is moved from the closed configuration to the open configuration, with the contours or profiles of the clip arms 130, 150 and/or the engaged features guiding movement of the clip arms 130, 150 relative to each other and the sleeve 110. According to various arrangements, each of the clip arms 130, 150 may include one or more straight segments (i.e., linear segments) having a straight profile and one or more curved segments (i.e., curvilinear segments) having a curved profile. As shown, each of the clip arms 130, 150 may include a plurality of straight segments and a plurality of curved segments, which define the overall contoured profiles of the clip arms 130, 150 for guiding movement of the clip arms 130, 150 relative to one another and the sleeve 110.

One or both of the clip arms 130, 150 may include one or more grasping features configured for engaging and grasping tissue of the gastrointestinal wall during use of the device 100. As shown, the first clip arm 130 may include a first claw 136 configured for engaging and grasping tissue, and the second clip arm 150 similarly may include a second claw 156 configured for engaging and grasping tissue. According to the illustrated example, the claws 136, 156 may be configured for engaging and grasping tissue of the mucosal layer of the gastrointestinal wall, as described below. As shown, the first claw 136 may be disposed at the distal end 134 of the first clip arm 130, and the second claw 156 may be disposed at the distal end 154 of the second clip arm 150. In this manner, the first claw 136 may define the distal end 134 of the first clip arm 130, and the second claw 156 may define the distal end 154 of the second clip arm 150. As shown, the claws 136, 156 may extend transverse to adjacent segments of the respective clip arms 130, 150. In some instances, the claws 136, 156 may extend perpendicular to the adjacent segments of the respective clip arms 130, 150. Various shapes and arrangements of the claws 136, 156 may be used.

FIGS. 1C and 1D illustrate an example use of the endoscopic clip device 100 for closure of a defect D in a gastrointestinal wall GW. The mucosal layer ML, the submucosal layer SML, the muscularis layer MSL, and the serosal layer SL of the gastrointestinal wall GW are shown in the figures. As shown, the defect D may be a mucosal defect extending into the mucosal layer ML of the gastrointestinal wall GW, without extending into the submucosal layer SML of the gastrointestinal wall GW. According to the illustrated example, the defect D may be a relatively small defect formed between a first margin FM and a second margin SM, with a width of the defect D between the first margin FM and the second margin SM being less than a distance between the distal ends 134, 154 of the clip arms 130, 150 when the clip 120 is in the open configuration. In other words, as shown in FIG. 1C, the clip 120 may be able to span the width of the defect D when the clip 120 is in the open configuration.

As discussed above, the device 100 may be advanced through an operative channel of an endoscope which may have a tortuous shape according to a location of the defect D within the gastrointestinal tract. Using a delivery device, the device 100 may be advanced through the operative channel while the clip 120 is in the closed configuration. In some instances, while the device 100 is advanced through the operative channel, a sheath of the delivery device may extend over and beyond the distal ends 134, 156 of the clip arms 130, 150 to prevent contact between the clip 120 and the operative channel. The device 100 may be advanced out of the operative channel to a location near but spaced apart from the defect D while the clip 120 remains in the closed configuration. The sheath may be retracted to expose the device 100, and then the clip 120 may be moved from the closed configuration to the open configuration. With the clip 120 in the open configuration, the device 100 may be positioned relative to the defect D such that the first claw 136 engages the first margin FM and the second claw 156 engages the second margin SM, as shown in FIG. 1C. The clip 120 then may be moved to the closed configuration to approximate the first margin FM and the second margin SM, grasping the engaged mucosal tissue therebetween and closing the defect D, as shown in FIG. 1D. According to the illustrated example, the claws 136, 156 may engage only the mucosal layer ML of the gastrointestinal wall GW to achieve closure of the defect D. In the event that the position of the device 100 relative to the defect D or the engagement between the clip 120 and the mucosal tissue is undesirable, the clip 120 may be moved to the open configuration, repositioned, and moved back to the closed configuration, if desired. After achieving a suitable position of the device 100 relative to the defect D and desired engagement between the clip 120 and the mucosal tissue, the device 100 may be deployed from the delivery device. In some instances, a plurality of the devices 100 may be used for closure of the defect D, depending on its size, with each of the devices 100 being used to approximate respective portions of the margins FM, SM and thus provide closure of a respective portion of the defect D.

Similar to existing TTS clip devices, the endoscopic clip device 100 may not be suitable for closure of a larger mucosal defect D because the clip 120 may be unable to span a width of the defect D when the clip 120 is in the open configuration. When the width of the defect D is greater than the distance between the distance between the distal ends 134, 154 of the clip arms 130, 150 when the clip 120 is in the open configuration, an alternative technique may be attempted but may not be successful for closing the large defect D. With the clip 120 in the open configuration, the distal end 134 of the first clip arm 130 may engage the first margin FM, and then the clip 120 may be moved to the closed configuration, such that the engaged mucosal tissue of the first margin FM is grasped between the claws 136, 156 of the clip arms 130, 150. Next, the device 100 may be used to pull the first margin FM toward the second margin SM while the clip 120 is in the closed configuration. The clip 120 then may be moved to the open configuration to allow the claw 156 of the second clip arm 150 to grasp the second margin SM, and the clip 120 subsequently may be moved back to the closed configuration to approximate the margins FM, SM, grasping the engaged mucosal tissue therebetween and closing the defect D. Although this technique may be suitable in some instances, a particular problem may arise when the clip 120 is moved to the open configuration to allow the second clip arm 150 to engage the second margin SM. Specifically, due to tension applied to the first margin FM when the first margin FM is pulled toward the second margin SM, the mucosal tissue of the first margin FM may slip off of the claw 136 of the first clip arm 130 when the clip 120 is moved to the open configuration. In other words, because of the applied tension, the first clip arm 130 may be unable to effectively grip the first margin FM when the clip 120 is moved to the open configuration. Certain embodiments of endoscopic clip devices described below may overcome this problem related to closure of large mucosal defects.

The endoscopic clip device 100 also may present additional problems when used to close a defect D that extends deeper than the mucosal layer ML of the gastrointestinal wall GW. For example, when a defect D extends into the submucosal layer SML, the muscularis layer MSL, or the serosal layer SL, the device 100 may be unable to approximate the opposing margins FM, SM of the defect D along these deeper layers of the gastrointestinal wall GW. In particular, although the device 100 may be able to approximate the margins along the mucosal layer ML, approximation of the deeper layers may not be possible because the clip arms 130, 150 may grasp only the mucosal tissue of the margins FM, SM. For these same reasons, the device 100 also may be unsuitable for closure of a transmural perforation in the gastrointestinal wall GW (i.e., a complete perforation extending through each of the mucosal, submucosal, muscularis, and serosal layers). Certain embodiments of endoscopic clip devices described below may overcome these problems related to closure of deep defects and transmural perforations.

Figure 2B:
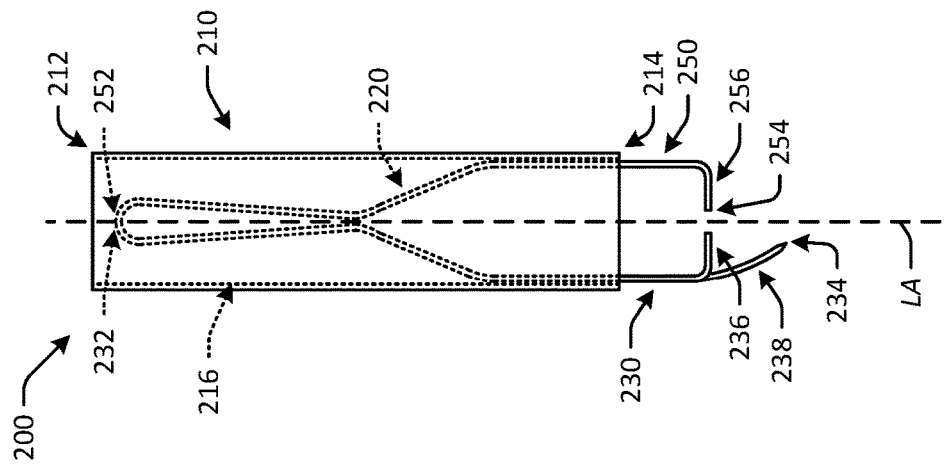
FIG. 2B is a side view of the endoscopic clip device of FIG. 2A, showing the clip in a closed configuration.
Figure 2A:
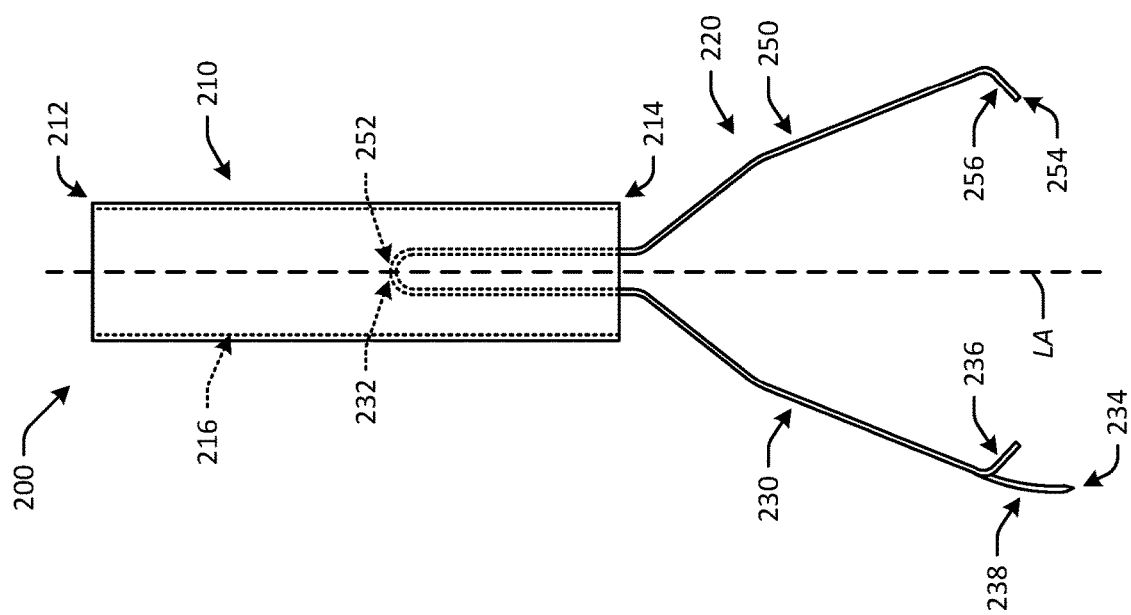
FIG. 2A is a side view of an example endoscopic clip device in accordance with embodiments of the disclosure, showing a sleeve and a clip of the endoscopic clip device, with the clip in an open configuration.

FIGS. 2A and 2B illustrate an example endoscopic clip device 200 (which also may be referred to as a "endoscopic device" or simply a "device") in accordance with embodiments of the present disclosure. The endoscopic clip device 200 may be configured to be advanced through an operative channel to a treatment site for closure of a defect, such as a mucosal defect, a defect, such as a mucosal defect, or a transmural perforation in a gastrointestinal wall of a patient. In some embodiments, the endoscopic clip device 200 may be advanced through an operative channel of an endoscope and thus may be considered to be a TTS clip device. In other embodiments, the endoscopic clip device 200 may be advanced through an operative channel of an overtube that is positioned over and used in conjunction with an endoscope and thus may not be considered to be a true "through-the-scope" clip device. FIGS. 2C-2J show the endoscopic clip device 200 being used for closure of defects D in a gastrointestinal wall GW in accordance with embodiments of the present disclosure, as discussed further below.

According to the example of FIGS. 2A and 2B, the endoscopic clip device 200 generally may include a sleeve 210 (which also may be referred to as a "shell" or a "capsule") and a clip 220 (which also may be referred to as an "endoscopic clip"). It will be appreciated that, in some embodiments, the device 200 also may include additional components other than the sleeve 210 and the clip 220, such as components that guide, control, or inhibit movement of the clip 220 relative to the sleeve 210 and/or components that facilitate interaction between the clip 220 or the sleeve 210 and mating components or features of a delivery device used to advance the device 200 through an operative channel of an endoscope or an overtube and subsequently deploy the device 200 within a patient's gastrointestinal tract. For simplicity of illustration, only the sleeve 210 and the clip 220 are shown in FIGS. 2A and 2B.

As shown in FIGS. 2A and 2B, the sleeve 210 may be formed as an elongated structure having a proximal end 212 and a distal end 214 disposed opposite one another along a longitudinal axis LA of the device 200. The longitudinal axis of the sleeve 210 may be coaxial with the longitudinal axis LA of the device 200. As shown, the sleeve 210 may define a passage 216 therein. In some embodiments, the passage 216 may extend from the proximal end 212 to the distal end 214 of the sleeve 210. In some embodiments, the sleeve 210 or at least a portion thereof may be formed as a tube having a cylindrical shape, although other shapes and configurations of the sleeve 210 may be used in other embodiments.

The clip 220 may be disposed at least partially within the sleeve 210 and may be coupled to the sleeve 210. As shown, a proximal portion of the clip 220 may be disposed within the passage 216 of the sleeve 210. According to different embodiments, various components and mechanisms may be used for coupling the clip 220 to the sleeve 210. As shown, the clip 220 may be configured for moving relative to the sleeve 210 between different configurations. According to the illustrated example, the clip 220 may be configured for reversibly moving relative to the sleeve 210 between an open configuration, as shown in FIG. 2A, and a closed configuration, as shown in FIG. 2B. The closed configuration of the clip 220 may be used for advancing the device 200 through an operative channel of an endoscope or an overtube to a treatment site and also for closing a defect in a gastrointestinal wall. The open configuration of the clip 220 may be used for positioning the device 200 relative to the gastrointestinal wall and for engaging tissue of the gastrointestinal wall with features of the clip 220 prior to closing the defect. As shown, the clip 220 may be reversibly moved between the open configuration and the closed configuration by translating the sleeve 210 relative to the clip 220 or translating the clip 220 relative to the sleeve 210 in the direction of the longitudinal axis LA of the device 200.

As shown in FIGS. 2A and 2B, the clip 220 generally may include a first clip arm 230 and a second clip arm 250 disposed opposite one another. In some instances, as shown, one or more corresponding portions of the clip arms 230, 250 may be centered on the longitudinal axis LA of the device 200. In some embodiments, as shown, the clip 220 may be asymmetric such that the first clip arm 230 and the second clip arm 250 are not mirror images of one another. As shown, the clip 220 may be asymmetric about a plane extending through the longitudinal axis LA of the device 200 and perpendicular to the views of FIGS. 2A and 2B. The first clip arm 230 may be formed as an elongated structure having a proximal end 232 and a distal end 234 disposed opposite one another in the direction of the longitudinal axis LA of the device 200. In a similar manner, the second clip arm 250 may be formed as an elongated structure having a proximal end 252 and a distal end 254 disposed opposite one another in the direction of the longitudinal axis LA of the device 200. As shown, the first clip arm 230 may have a first length between the proximal end 232 and the distal end 234 in the direction of the longitudinal axis LA of the device 200, and the second clip arm 250 may have a second length between the proximal end 252 and the distal end 254 in the direction of the longitudinal axis LA of the device 200. In some embodiments, as shown, the first length may be different from the second length when the clip 220 is in the open configuration and when the clip 220 is in the closed configuration. In some embodiments, as shown, the first length may be greater than the second length. In some embodiments, as shown, the proximal end 232 of the first clip arm 230 may be coupled to the proximal end 252 of the second clip arm 250. In some embodiments, as shown, the first clip arm 230 and the second clip arm 250 may be integrally formed with one another, with the proximal end 232 of the first clip arm 230 being directly coupled to the proximal end 252 of the second clip arm 250. In other embodiments, the first clip arm 230 and the second clip arm 250 may be coupled to one another by one or more additional portions or components of the clip 220 which are separately formed and attached to the clip arms 230, 250. Various arrangements of the clip arms 230, 250 and the overall clip 220 may be used in different embodiments.

As shown, the proximal ends 232, 252 of the clip arms 230, 250 may be disposed within the passage 216 of the sleeve 210 when the clip 220 is in the open configuration and when the clip 220 is in the closed configuration. In contrast, the distal ends 234, 254 of the clip arms 230, 250 may be disposed outside of the passage 216 of the sleeve 210 when the clip 220 is in the open configuration and when the clip 220 is in the closed configuration. As shown, the distal ends 234, 254 of the clip arms 230, 250 may move toward one another when the clip 220 is moved from the open configuration to the closed configuration, and the distal ends 234, 254 of the clip arms 230, 250 may move away from one another when the clip 220 is moved from the closed configuration to the open configuration. Various contours or profiles of the clip arms 230, 250, as shown in the views of FIGS. 2A and 2B, may be used in different embodiments. The contours or profiles of the clip arms 230, 250 may dictate how the clip arms 230, 250 move relative to each other and the sleeve 210 when the clip 220 is moved between the open configuration and the closed configuration. In some embodiments, the clip arms 230, 250 may engage one or more features of the sleeve 210 when the clip 220 is moved from the open configuration to the closed configuration and/or when the clip 220 is moved from the closed configuration to the open configuration, with the contours or profiles of the clip arms 230, 250 and/or the engaged features guiding movement of the clip arms 230, 250 relative to each other and the sleeve 210. In some instances, the clip arms 230, 250 additionally or alternatively may engage one or more features of other components of the device 200 (i.e., other than the sleeve 210) when the clip 220 is moved from the open configuration to the closed configuration and/or when the clip 220 is moved from the closed configuration to the open configuration, with the contours or profiles of the clip arms 230, 250 and/or the engaged features guiding movement of the clip arms 230, 250 relative to each other and the sleeve 210. According to various arrangements, each of the clip arms 230, 250 may include one or more straight segments (i.e., linear segments) having a straight profile and one or more curved segments (i.e., curvilinear segments) having a curved profile. As shown, each of the clip arms 230, 250 may include a plurality of straight segments and a plurality of curved segments, which define the overall contoured profiles of the clip arms 230, 250 for guiding movement of the clip arms 230, 250 relative to one another and the sleeve 210.

One or both of the clip arms 230, 250 may include one or more grasping features configured for engaging and grasping tissue of the gastrointestinal wall during use of the device 200. As shown, the first clip arm 230 may include a first claw 236 configured for engaging and grasping tissue, and the second clip arm 250 similarly may include a second claw 256 configured for engaging and grasping tissue. According to the illustrated example, the claws 236, 256 may be configured for engaging and grasping tissue of the mucosal layer of the gastrointestinal wall, as described below. As shown, the first claw 236 may be spaced apart from the distal end 234 of the first clip arm 230, while the second claw 256 may be disposed at the distal end 254 of the second clip arm 250. In this manner, the second claw 256 may define the distal end 254 of the second clip arm 250. As shown, the claws 236, 256 may extend transverse to adjacent segments of the respective clip arms 230, 250. In some embodiments, the claws 236, 256 may extend perpendicular to the adjacent segments of the respective clip arms 230, 250. Various shapes and arrangements of the claws 236, 256 may be used in different embodiments.

According to the illustrated example, the first clip arm 230 also may include a needle 238 (which also may be referred to as an "anchor" or an "extension") configured for engaging and grasping tissue. As shown, the needle 238 may extend to the distal end 234 of the first clip arm 230. In this manner, the needle 238 may define the distal end 234 of the first clip arm 230. As shown, the needle 238 may extend beyond the first claw 236, with the first claw 236 extending transverse to the needle 238. In some embodiments, as shown, at least a portion of the needle 238 may have a curved shape. For example, a distal portion of the needle 238 extending to the distal end 234 of the first clip arm 230 may have a curved shape, as shown. In some embodiments, an entirety of the needle 238 may have a curved shape. In other embodiments, at least a portion of the needle 238 may have a straight shape. For example, a distal portion of the needle 238 extending to the distal end 234 of the first clip arm 230 may have a straight shape. Various shapes of the needle 238 may be used in different embodiments. In some embodiments, the needle 238 may be configured for advancing through the mucosal layer and into at least the submucosal layer of the gastrointestinal wall. In some embodiments, the needle 238 may be configured for advancing through the mucosal layer and the submucosal layer and into at least the muscularis layer of the gastrointestinal wall. In some embodiments, the needle 238 may be configured for advancing through the mucosal layer, the submucosal layer, and the muscularis layer and into the serosal layer of the gastrointestinal wall. As shown, the distal tip of the needle 238 may be pointed or otherwise sharpened to facilitate insertion of the needle 238 into and through tissue. In some embodiments, the needle 238 may include one or more retention features configured for retaining the needle 238 within tissue into which the needle 238 is inserted, thereby inhibiting or preventing removal of the needle 238 from the engaged tissue. For example, the needle 239 may include one or more barbs, one or more serrations, or one or more other retention features, which may be spaced apart from the distal end 234 of the first clip arm 230. In some embodiments, the needle 238 may include an arrowhead tip disposed at the distal end 234 of the first clip arm 230 and configured for retaining the needle 238 within engaged tissue. As discussed below, the needle 238 may be used to facilitate closure of large defects as well as deep defects in the gastrointestinal wall.

FIGS. 2C and 2D illustrate an example use of the endoscopic clip device 200 for closure of a defect D in a gastrointestinal wall GW in accordance with embodiments of the present disclosure. The mucosal layer ML, the submucosal layer SML, the muscularis layer MSL, and the serosal layer SL of the gastrointestinal wall GW are shown in the figures. As shown, the defect D may be a mucosal defect extending into the mucosal layer ML of the gastrointestinal wall GW, without extending into the submucosal layer SML of the gastrointestinal wall GW. According to the illustrated example, the defect D may be a relatively small defect formed between a first margin FM and a second margin SM, with a width of the defect D between the first margin FM and the second margin SM being less than a distance between the distal ends 234, 254 of the clip arms 230, 250 when the clip 220 is in the open configuration. In other words, as shown in FIG. 2C, the clip 220 may be able to span the width of the defect D when the clip 220 is in the open configuration.

As discussed above, the device 200 may be advanced through an operative channel of an endoscope or an overtube which may have a tortuous shape according to a location of the defect D within the gastrointestinal tract. Using a delivery device, the device 200 may be advanced through the operative channel while the clip 220 is in the closed configuration. In some instances, while the device 200 is advanced through the operative channel, a sheath of the delivery device may extend over and beyond the distal ends 234, 256 of the clip arms 230, 250 to prevent contact between the clip 220 and the operative channel. The device 200 may be advanced out of the operative channel to a location near but spaced apart from the defect D while the clip 220 remains in the closed configuration. The sheath may be retracted to expose the device 200, and then the clip 220 may be moved from the closed configuration to the open configuration. With the clip 220 in the open configuration, the device 200 may be positioned relative to the defect D and the needle 238 may be advanced into the first margin FM, as shown in FIG. 2C. As shown, the needle 238 may be advanced through the mucosal layer ML and into at least the submucosal layer SML. In different embodiments, the needle 238 may be advanced into the muscularis layer MSL or into the serosal layer SL. In some embodiments, as shown, the device 200 may be positioned such that the first claw 236 engages the first margin FM and the second claw 256 engages the second margin SM. The clip 220 then may be moved to the closed configuration to approximate the first margin FM and the second margin SM, grasping the engaged mucosal tissue therebetween and closing the defect D, as shown in FIG. 2D. In some embodiments, as shown, as the clip 220 is moved from the open configuration to the closed configuration, the needle 238 may be advanced deeper into the gastrointestinal wall GW. According to the illustrated example, the claws 236, 256 may engage only the mucosal layer ML of the gastrointestinal wall GW. In the event that the position of the device 200 relative to the defect D or the engagement between the clip 220 and the tissue is undesirable, the clip 220 may be moved to the open configuration, repositioned, and moved back to the closed configuration, if desired. After achieving a suitable position of the device 200 relative to the defect D and desired engagement between the clip 220 and the mucosal tissue, the device 200 may be deployed from the delivery device. In some instances, a plurality of the devices 200 may be used for closure of the defect D, depending on its size, with each of the devices 200 being used to approximate respective portions of the margins FM, SM and thus provide closure of a respective portion of the defect D.

FIGS. 2E-2J illustrate another example use of the endoscopic clip device 200 for closure of a larger defect D in a gastrointestinal wall GW in accordance with embodiments of the present disclosure. The illustrated technique may be employed when the width of the defect D is greater than the distance between the distance between the distal ends 234, 254 of the clip arms 230, 250 when the clip 220 is in the open configuration. With the clip 220 in the open configuration, the needle 238 may be advanced into the mucosal layer ML, as shown in FIG. 2E. The clip 220 then may be moved to the closed configuration, as shown in FIG. 2F. Next, as shown in FIG. 2G, the device 200 may be used to pull the first margin FM toward the second margin SM while the clip 220 is in the closed configuration, while the needle 238 remains engaged with the first margin FM, thereby approximating the first margin FM and the second margin SM. With the needle 238 positioned adjacent the second margin SM, the needle 238 may be further advanced into the gastrointestinal wall GW to secure the margins FM, SM, as shown in FIG. 2H. In some embodiments, as shown, the needle 238 may be advanced through the mucosal layer ML and into the submucosal layer SML. In different embodiments, the needle 238 may be advanced into the muscularis layer MSL or into the serosal layer SL. Next, the clip 220 may be moved from the closed configuration to the open configuration, as shown in FIG. 2I, thereby repositioning the claws 236, 238 relative to the tissue. As shown in FIG. 2J, the clip 220 then may be moved from the open configuration to the closed configuration such that the claws 236, 238 engage and grasp the mucosal tissue therebetween, securing closure of the defect D.

Although the example of FIGS. 2A and 2B and the example of FIGS. 2E-2J show the device 200 being used for closure of a mucosal defect, the device 200 may be used in a similar manner for closure of a defect D that extends deeper than the mucosal layer ML of the gastrointestinal wall GW. For example, when a defect D extends into the submucosal layer SML, the muscularis layer MSL, or the serosal layer SL, the deep engagement provided by the needle 238 of the device 200 in combination with the engagement of the mucosal tissue with the claws 236, 238 may provide approximation of the opposing margins FM, SM of the defect D along the deeper layers of the gastrointestinal wall GW. For these same reasons, in some embodiments, the device 200 also may be suitable for closure of a transmural perforation in the gastrointestinal wall GW.

Figures 3E, 3F:
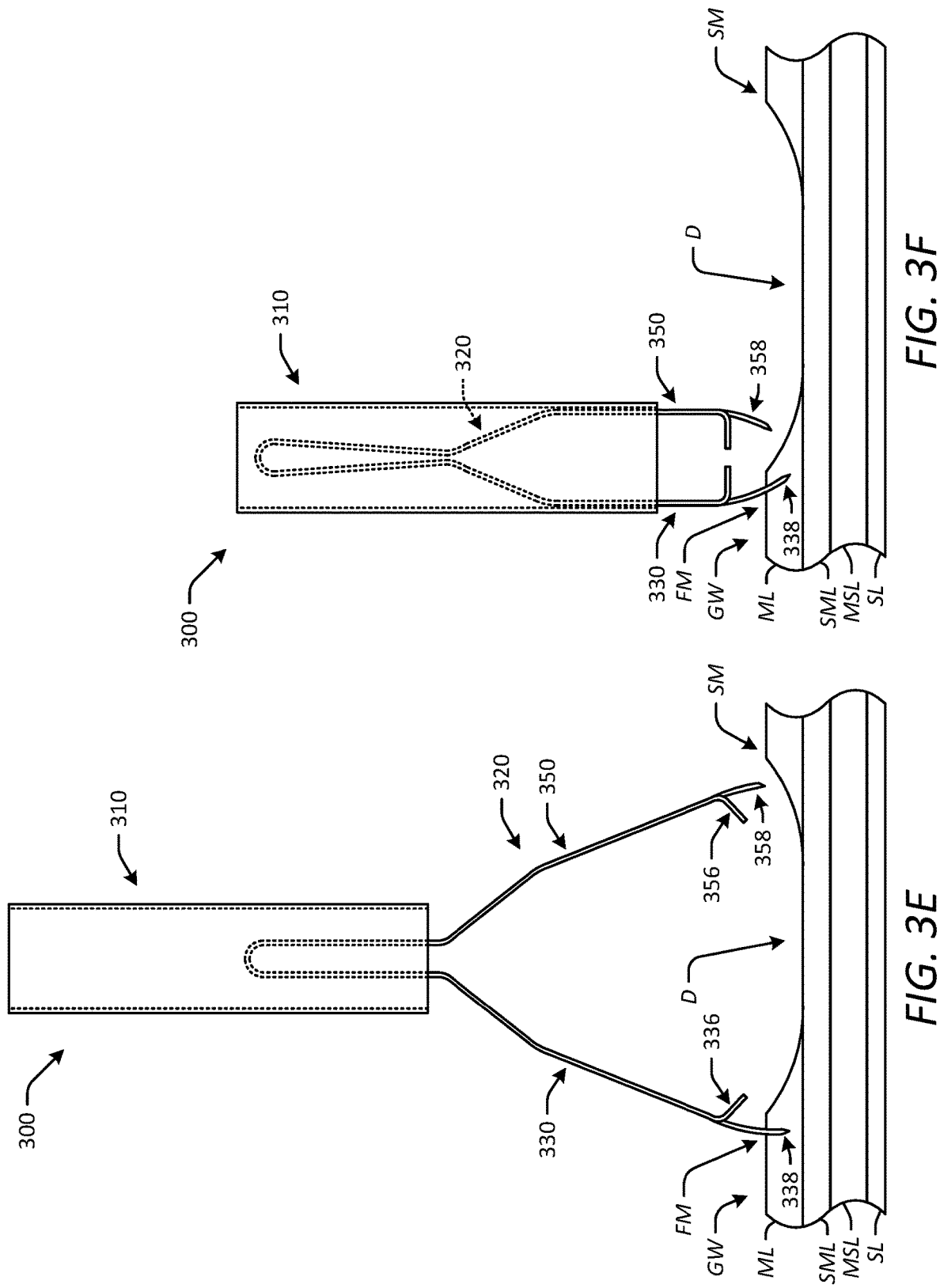

FIGS. 3A and 3B illustrate an example endoscopic clip device 300 (which also may be referred to as a "endoscopic device" or simply a "device") in accordance with embodiments of the present disclosure. The endoscopic clip device 300 may be configured to be advanced through an operative channel to a treatment site for closure of a defect, such as a mucosal defect, a defect, such as a mucosal defect, or a transmural perforation in a gastrointestinal wall of a patient. In some embodiments, the endoscopic clip device 300 may be advanced through an operative channel of an endoscope and thus may be considered to be a TTS clip device. In other embodiments, the endoscopic clip device 300 may be advanced through an operative channel of an overtube that is positioned over and used in conjunction with an endoscope and thus may not be considered to be a true "through-the-scope" clip device. FIGS. 3C-3J show the endoscopic clip device 300 being used for closure of defects D in a gastrointestinal wall GW in accordance with embodiments of the present disclosure, as discussed further below.

According to the example of FIGS. 3A and 3B, the endoscopic clip device 300 generally may include a sleeve 310 (which also may be referred to as a "shell" or a "capsule") and a clip 320 (which also may be referred to as an "endoscopic clip"). It will be appreciated that, in some embodiments, the device 300 also may include additional components other than the sleeve 310 and the clip 320, such as components that guide, control, or inhibit movement of the clip 320 relative to the sleeve 310 and/or components that facilitate interaction between the clip 320 or the sleeve 310 and mating components or features of a delivery device used to advance the device 300 through an operative channel of an endoscope or an overtube and subsequently deploy the device 300 within a patient's gastrointestinal tract. For simplicity of illustration, only the sleeve 310 and the clip 320 are shown in FIGS. 3A and 3B.

As shown in FIGS. 3A and 3B, the sleeve 310 may be formed as an elongated structure having a proximal end 312 and a distal end 314 disposed opposite one another along a longitudinal axis LA of the device 300. The longitudinal axis of the sleeve 310 may be coaxial with the longitudinal axis LA of the device 300. As shown, the sleeve 310 may define a passage 316 therein. In some embodiments, the passage 316 may extend from the proximal end 312 to the distal end 314 of the sleeve 310. In some embodiments, the sleeve 310 or at least a portion thereof may be formed as a tube having a cylindrical shape, although other shapes and configurations of the sleeve 310 may be used in other embodiments.

The clip 320 may be disposed at least partially within the sleeve 310 and may be coupled to the sleeve 310. As shown, a proximal portion of the clip 320 may be disposed within the passage 316 of the sleeve 310. According to different embodiments, various components and mechanisms may be used for coupling the clip 320 to the sleeve 310. As shown, the clip 320 may be configured for moving relative to the sleeve 310 between different configurations. According to the illustrated example, the clip 320 may be configured for reversibly moving relative to the sleeve 310 between an open configuration, as shown in FIG. 3A, and a closed configuration, as shown in FIG. 3B. The closed configuration of the clip 320 may be used for advancing the device 300 through an operative channel of an endoscope or an overtube to a treatment site and also for closing a defect in a gastrointestinal wall. The open configuration of the clip 320 may be used for positioning the device 200 relative to the gastrointestinal wall and for engaging tissue of the gastrointestinal wall with features of the clip 320 prior to closing the defect. As shown, the clip 320 may be reversibly moved between the open configuration and the closed configuration by translating the sleeve 310 relative to the clip 320 or translating the clip 320 relative to the sleeve 310 in the direction of the longitudinal axis LA of the device 300.

As shown in FIGS. 3A and 3B, the clip 320 generally may include a first clip arm 330 and a second clip arm 350 disposed opposite one another. In some instances, as shown, one or more corresponding portions of the clip arms 330, 350 may be centered on the longitudinal axis LA of the device 300 In some embodiments, as shown, the clip 320 may be asymmetric such that the first clip arm 330 and the second clip arm 350 are not mirror images of one another. As shown, the clip 320 may be asymmetric about a plane extending through the longitudinal axis LA of the device 300 and perpendicular to the views of FIGS. 3A and 3B. The first clip arm 330 may be formed as an elongated structure having a proximal end 332 and a distal end 334 disposed opposite one another in the direction of the longitudinal axis LA of the device 300. In a similar manner, the second clip arm 350 may be formed as an elongated structure having a proximal end 352 and a distal end 354 disposed opposite one another in the direction of the longitudinal axis LA of the device 300. As shown, the first clip arm 330 may have a first length between the proximal end 332 and the distal end 334 in the direction of the longitudinal axis LA of the device 300, and the second clip arm 350 may have a second length between the proximal end 352 and the distal end 354 in the direction of the longitudinal axis LA of the device 300. In some embodiments, as shown, the first length may be different from the second length when the clip 320 is in the open configuration and when the clip 320 is in the closed configuration. In some embodiments, as shown, the first length may be greater than the second length. In some embodiments, as shown, the proximal end 332 of the first clip arm 330 may be coupled to the proximal end 352 of the second clip arm 350. In some embodiments, as shown, the first clip arm 330 and the second clip arm 350 may be integrally formed with one another, with the proximal end 332 of the first clip arm 330 being directly coupled to the proximal end 352 of the second clip arm 350. In other embodiments, the first clip arm 330 and the second clip arm 350 may be coupled to one another by one or more additional portions or components of the clip 320 which are separately formed and attached to the clip arms 330, 350. Various arrangements of the clip arms 330, 350 and the overall clip 320 may be used in different embodiments.

As shown, the proximal ends 332, 352 of the clip arms 330, 350 may be disposed within the passage 316 of the sleeve 310 when the clip 320 is in the open configuration and when the clip 320 is in the closed configuration. In contrast, the distal ends 334, 354 of the clip arms 330, 350 may be disposed outside of the passage 316 of the sleeve 310 when the clip 320 is in the open configuration and when the clip 320 is in the closed configuration. As shown, the distal ends 334, 354 of the clip arms 330, 350 may move toward one another when the clip 320 is moved from the open configuration to the closed configuration, and the distal ends 334, 354 of the clip arms 330, 350 may move away from one another when the clip 320 is moved from the closed configuration to the open configuration. Various contours or profiles of the clip arms 330, 350, as shown in the views of FIGS. 3A and 3B, may be used in different embodiments. The contours or profiles of the clip arms 330, 350 may dictate how the clip arms 330, 350 move relative to each other and the sleeve 310 when the clip 320 is moved between the open configuration and the closed configuration. In some embodiments, the clip arms 330, 350 may engage one or more features of the sleeve 310 when the clip 320 is moved from the open configuration to the closed configuration and/or when the clip 320 is moved from the closed configuration to the open configuration, with the contours or profiles of the clip arms 330, 350 and/or the engaged features guiding movement of the clip arms 330, 350 relative to each other and the sleeve 310. In some instances, the clip arms 330, 350 additionally or alternatively may engage one or more features of other components of the device 300 (i.e., other than the sleeve 310) when the clip 320 is moved from the open configuration to the closed configuration and/or when the clip 320 is moved from the closed configuration to the open configuration, with the contours or profiles of the clip arms 330, 350 and/or the engaged features guiding movement of the clip arms 330, 350 relative to each other and the sleeve 310. According to various arrangements, each of the clip arms 330, 350 may include one or more straight segments (i.e., linear segments) having a straight profile and one or more curved segments (i.e., curvilinear segments) having a curved profile. As shown, each of the clip arms 330, 350 may include a plurality of straight segments and a plurality of curved segments, which define the overall contoured profiles of the clip arms 330, 350 for guiding movement of the clip arms 330, 350 relative to one another and the sleeve 310.

One or both of the clip arms 330, 350 may include one or more grasping features configured for engaging and grasping tissue of the gastrointestinal wall during use of the device 300. As shown, the first clip arm 330 may include a first claw 336 configured for engaging and grasping tissue, and the second clip arm 350 similarly may include a second claw 356 configured for engaging and grasping tissue. According to the illustrated example, the claws 336, 356 may be configured for engaging and grasping tissue of the mucosal layer of the gastrointestinal wall, as described below. As shown, the first claw 336 may be spaced apart from the distal end 334 of the first clip arm 330, and the second claw 356 may be spaced apart from the distal end 354 of the second clip arm 350. As shown, the claws 336, 356 may extend transverse to adjacent segments of the respective clip arms 330, 350. In some embodiments, the claws 336, 356 may extend perpendicular to the adjacent segments of the respective clip arms 330, 350. Various shapes and arrangements of the claws 336, 356 may be used in different embodiments.

According to the illustrated example, the first clip arm 330 also may include a first needle 338 (which also may be referred to as a "first anchor" or a "first extension") configured for engaging and grasping tissue, and the second clip arm 350 also may include a second needle 358 (which also may be referred to as a "second anchor" or a "second extension") configured for engaging and grasping tissue. As shown, the first needle 338 may extend to the distal end 334 of the first clip arm 330, and the second needle 358 may extend to the distal end 354 of the second clip arm 350. In this manner, the first needle 338 may define the distal end 334 of the first clip arm 330, and the second needle 358 may define the distal end 354 of the second clip arm 350. As shown, the first needle 338 may extend beyond the first claw 336, with the first claw 336 extending transverse to the first needle 338. Similarly, the second needle 358 may extend beyond the second claw 356, with the second claw 356 extending transverse to the second needle 358. In some embodiments, as shown, at least a portion of each of the needles 338, 358 may have a curved shape. For example, a distal portion of each of the needles 338, 358 extending to the respective distal ends 334, 354 of the clip arms 330, 350 may have a curved shape, as shown. In some embodiments, an entirety of each of the needles 338, 358 may have a curved shape. In other embodiments, at least a portion of each of the needles 338, 358 may have a straight shape. For example, a distal portion of each of the needles 338, 358 extending to the respective distal ends 334, 354 of the clip arms 330 may have a straight shape. Various shapes of the needles 338, 358 may be used in different embodiments. In some embodiments, at least one, or both, of the needles 338, 358 may be configured for advancing through the mucosal layer and into at least the submucosal layer of the gastrointestinal wall. In some embodiments, at least one, or both, of the needles 338, 358 may be configured for advancing through the mucosal layer and the submucosal layer and into at least the muscularis layer of the gastrointestinal wall. In some embodiments, at least one, or both, of the needles 338, 358 may be configured for advancing through the mucosal layer, the submucosal layer, and the muscularis layer and into the serosal layer of the gastrointestinal wall. As shown, the distal tips of the needles 338, 358 may be pointed or otherwise sharpened to facilitate insertion of the needles 338, 358 into and through tissue. In some embodiments, the needles 338, 358 may include one or more retention features configured for retaining the needles 338, 358 within tissue into which the needles 338, 358 are inserted, thereby inhibiting or preventing removal of the needles 338, 358 from the engaged tissue. For example, at least one, or both, of needles 338, 358 may include one or more barbs, one or more serrations, or one or more other retention features, which may be spaced apart from the respective distal ends 334, 354 of the clip arms 330, 350. In some embodiments, at least one, or both, of needles 338, 358 may include an arrowhead tip disposed at the respective distal ends 334, 354 of the clip arms 330, 350 and configured for retaining the needles 338, 358 within engaged tissue. As discussed below, the needles 338, 358 may be used to facilitate closure of large defects as well as deep defects in the gastrointestinal wall.

FIGS. 3C and 3D illustrate an example use of the endoscopic clip device 300 for closure of a defect D in a gastrointestinal wall GW in accordance with embodiments of the present disclosure. The mucosal layer ML, the submucosal layer SML, the muscularis layer MSL, and the serosal layer SL of the gastrointestinal wall GW are shown in the figures. As shown, the defect D may be a mucosal defect extending into the mucosal layer ML of the gastrointestinal wall GW, without extending into the submucosal layer SML of the gastrointestinal wall GW. According to the illustrated example, the defect D may be a relatively small defect formed between a first margin FM and a second margin SM, with a width of the defect D between the first margin FM and the second margin SM being less than a distance between the distal ends 334, 354 of the clip arms 330, 350 when the clip 320 is in the open configuration. In other words, as shown in FIG. 3C, the clip 320 may be able to span the width of the defect D when the clip 320 is in the open configuration.

As discussed above, the device 300 may be advanced through an operative channel of an endoscope or an overtube which may have a tortuous shape according to a location of the defect D within the gastrointestinal tract. Using a delivery device, the device 300 may be advanced through the operative channel while the clip 320 is in the closed configuration. In some instances, while the device 300 is advanced through the operative channel, a sheath of the delivery device may extend over and beyond the distal ends 334, 356 of the clip arms 330, 350 to prevent contact between the clip 320 and the operative channel. The device 300 may be advanced out of the operative channel to a location near but spaced apart from the defect D while the clip 320 remains in the closed configuration. The sheath may be retracted to expose the device 300, and then the clip 320 may be moved from the closed configuration to the open configuration. With the clip 320 in the open configuration, the device 300 may be positioned relative to the defect D, the first needle 338 may be advanced into the first margin FM, and the second needle 358 may be advanced into the second margin SM, as shown in FIG. 3C. As shown, the first needle 338 may be advanced through the mucosal layer ML and into at least the submucosal layer SML, and the second needle 358 may be advanced into the mucosal layer ML. In different embodiments, the first needle 338 may be advanced into the muscularis layer MSL or into the serosal layer SL. In some embodiments, as shown, the device 300 may be positioned such that the first claw 336 engages the first margin FM and the second claw 356 engages the second margin SM. The clip 320 then may be moved to the closed configuration to approximate the first margin FM and the second margin SM, grasping the engaged mucosal tissue therebetween and closing the defect D, as shown in FIG. 3D. In some embodiments, as shown, as the clip 320 is moved from the open configuration to the closed configuration, the needles 338, 358 may be advanced deeper into the gastrointestinal wall GW. According to the illustrated example, the claws 336, 356 may engage only the mucosal layer ML of the gastrointestinal wall GW. In the event that the position of the device 300 relative to the defect D or the engagement between the clip 320 and the tissue is undesirable, the clip 320 may be moved to the open configuration, repositioned, and moved back to the closed configuration, if desired. After achieving a suitable position of the device 300 relative to the defect D and desired engagement between the clip 320 and the mucosal tissue, the device 300 may be deployed from the delivery device. In some instances, a plurality of the devices 300 may be used for closure of the defect D, depending on its size, with each of the devices 300 being used to approximate respective portions of the margins FM, SM and thus provide closure of a respective portion of the defect D.

FIGS. 3E-3J illustrate another example use of the endoscopic clip device 300 for closure of a larger defect D in a gastrointestinal wall GW in accordance with embodiments of the present disclosure. The illustrated technique may be employed when the width of the defect D is greater than the distance between the distance between the distal ends 334, 354 of the clip arms 330, 350 when the clip 320 is in the open configuration. With the clip 320 in the open configuration, the first needle 338 may be advanced into the mucosal layer ML, as shown in FIG. 3E. The clip 320 then may be moved to the closed configuration, as shown in FIG. 3F. Next, as shown in FIG. 3G, the device 300 may be used to pull the first margin FM toward the second margin SM while the clip 320 is in the closed configuration, while the first needle 338 remains engaged with the first margin FM, thereby approximating the first margin FM and the second margin SM. With the first needle 338 positioned adjacent the second margin SM, the first needle 338 may be further advanced into the gastrointestinal wall GW to secure the margins FM, SM, as shown in FIG. 3H. In some embodiments, as shown, the first needle 338 may be advanced through the mucosal layer ML and into the submucosal layer SML. In different embodiments, the first needle 338 may be advanced into the muscularis layer MSL or into the serosal layer SL. Next, the clip 320 may be moved from the closed configuration to the open configuration, as shown in FIG. 3I, thereby repositioning the claws 336, 338 and the second needle 358 relative to the tissue. In some embodiments, the second needle 358 may be inserted into the second margin SM when the clip 320 is moved to the closed configuration in FIG. 3H, and as the clip 320 is moved from the closed configuration to the open configuration, the second needle 358 may be withdrawn from and the reinserted into the second margin SM, as shown in FIG. 3I. As shown in FIG. 3J, the clip 320 then may be moved from the open configuration to the closed configuration such that the claws 336, 338 engage and grasp the mucosal tissue therebetween, securing closure of the defect D.

Although the example of FIGS. 3A and 3B and the example of FIGS. 3E-3J show the device 300 being used for closure of a mucosal defect, the device 300 may be used in a similar manner for closure of a defect D that extends deeper than the mucosal layer ML of the gastrointestinal wall GW. For example, when a defect D extends into the submucosal layer SML, the muscularis layer MSL, or the serosal layer SL, the deep engagement provided by the needles 338, 358 of the device 300 in combination with the engagement of the mucosal tissue with the claws 336, 338 may provide approximation of the opposing margins FM, SM of the defect D along the deeper layers of the gastrointestinal wall GW. For these same reasons, in some embodiments, the device 300 also may be suitable for closure of a transmural perforation in the gastrointestinal wall GW.

Figure 4B:
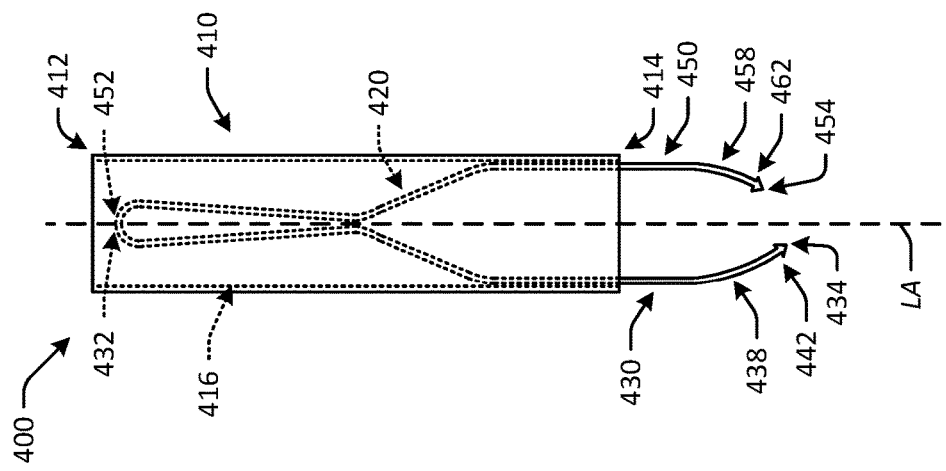
FIG. 4B is a side view of the endoscopic clip device of FIG. 4A, showing the clip in a closed configuration.
Figure 4A:
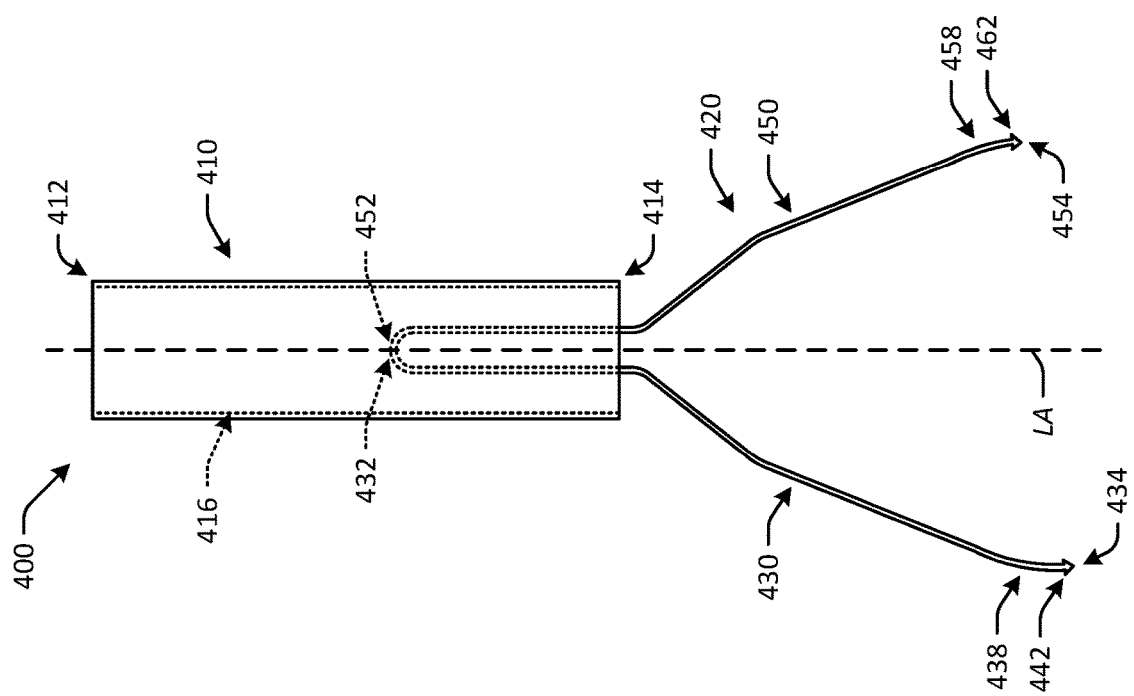
FIG. 4A is a side view of an example endoscopic clip device in accordance with embodiments of the disclosure, showing a sleeve and a clip of the endoscopic clip device, with the clip in an open configuration.

FIGS. 4A and 4B illustrate an example endoscopic clip device 400 (which also may be referred to as a "endoscopic device" or simply a "device") in accordance with embodiments of the present disclosure. The endoscopic clip device 400 may be configured to be advanced through an operative channel to a treatment site for closure of a defect, such as a mucosal defect, or a transmural perforation in a gastrointestinal wall of a patient. In some embodiments, the endoscopic clip device 400 may be advanced through an operative channel of an endoscope and thus may be considered to be a TTS clip device. In other embodiments, the endoscopic clip device 400 may be advanced through an operative channel of an overtube that is positioned over and used in conjunction with an endoscope and thus may not be considered to be a true "through-the-scope" clip device. FIGS. 4C-4J show the endoscopic clip device 400 being used for closure of defects D in a gastrointestinal wall GW in accordance with embodiments of the present disclosure, as discussed further below.

According to the example of FIGS. 4A and 4B, the endoscopic clip device 400 generally may include a sleeve 410 (which also may be referred to as a "shell" or a "capsule") and a clip 420 (which also may be referred to as an "endoscopic clip"). It will be appreciated that, in some embodiments, the device 400 also may include additional components other than the sleeve 410 and the clip 420, such as components that guide, control, or inhibit movement of the clip 420 relative to the sleeve 410 and/or components that facilitate interaction between the clip 420 or the sleeve 410 and mating components or features of a delivery device used to advance the device 400 through an operative channel of an endoscope or an overtube and subsequently deploy the device 400 within a patient's gastrointestinal tract. For simplicity of illustration, only the sleeve 410 and the clip 420 are shown in FIGS. 4A and 4B.

As shown in FIGS. 4A and 4B, the sleeve 410 may be formed as an elongated structure having a proximal end 412 and a distal end 414 disposed opposite one another along a longitudinal axis LA of the device 400. The longitudinal axis of the sleeve 410 may be coaxial with the longitudinal axis LA of the device 300. As shown, the sleeve 410 may define a passage 416 therein. In some embodiments, the passage 416 may extend from the proximal end 412 to the distal end 414 of the sleeve 410. In some embodiments, the sleeve 410 or at least a portion thereof may be formed as a tube having a cylindrical shape, although other shapes and configurations of the sleeve 410 may be used in other embodiments.

The clip 420 may be disposed at least partially within the sleeve 410 and may be coupled to the sleeve 410. As shown, a proximal portion of the clip 420 may be disposed within the passage 416 of the sleeve 410. According to different embodiments, various components and mechanisms may be used for coupling the clip 420 to the sleeve 410. As shown, the clip 420 may be configured for moving relative to the sleeve 410 between different configurations. According to the illustrated example, the clip 420 may be configured for reversibly moving relative to the sleeve 410 between an open configuration, as shown in FIG. 4A, and a closed configuration, as shown in FIG. 4B. The closed configuration of the clip 420 may be used for advancing the device 400 through an operative channel of an endoscope or an overtube to a treatment site and also for closing a defect in a gastrointestinal wall. The open configuration of the clip 420 may be used for positioning the device 400 relative to the gastrointestinal wall and for engaging tissue of the gastrointestinal wall with features of the clip 420 prior to closing the defect. As shown, the clip 420 may be reversibly moved between the open configuration and the closed configuration by translating the sleeve 410 relative to the clip 420 or translating the clip 420 relative to the sleeve 410 in the direction of the longitudinal axis LA of the device 400.

As shown in FIGS. 4A and 4B, the clip 420 generally may include a first clip arm 430 and a second clip arm 450 disposed opposite one another. In some instances, as shown, one or more corresponding portions of the clip arms 430, 450 may be centered on the longitudinal axis LA of the device 400 In some embodiments, as shown, the clip 420 may be asymmetric such that the first clip arm 430 and the second clip arm 450 are not mirror images of one another. As shown, the clip 420 may be asymmetric about a plane extending through the longitudinal axis LA of the device 400 and perpendicular to the views of FIGS. 4A and 4B. The first clip arm 430 may be formed as an elongated structure having a proximal end 432 and a distal end 434 disposed opposite one another in the direction of the longitudinal axis LA of the device 400. In a similar manner, the second clip arm 450 may be formed as an elongated structure having a proximal end 452 and a distal end 454 disposed opposite one another in the direction of the longitudinal axis LA of the device 400. As shown, the first clip arm 430 may have a first length between the proximal end 432 and the distal end 434 in the direction of the longitudinal axis LA of the device 400, and the second clip arm 450 may have a second length between the proximal end 452 and the distal end 454 in the direction of the longitudinal axis LA of the device 400. In some embodiments, as shown, the first length may be different from the second length when the clip 420 is in the open configuration and when the clip 420 is in the closed configuration. In some embodiments, as shown, the first length may be greater than the second length. In some embodiments, as shown, the proximal end 432 of the first clip arm 430 may be coupled to the proximal end 452 of the second clip arm 450. In some embodiments, as shown, the first clip arm 430 and the second clip arm 450 may be integrally formed with one another, with the proximal end 432 of the first clip arm 430 being directly coupled to the proximal end 452 of the second clip arm 450. In other embodiments, the first clip arm 430 and the second clip arm 450 may be coupled to one another by one or more additional portions or components of the clip 420 which are separately formed and attached to the clip arms 430, 450. Various arrangements of the clip arms 430, 450 and the overall clip 420 may be used in different embodiments.

As shown, the proximal ends 432, 452 of the clip arms 430, 450 may be disposed within the passage 416 of the sleeve 410 when the clip 420 is in the open configuration and when the clip 420 is in the closed configuration. In contrast, the distal ends 434, 454 of the clip arms 430, 450 may be disposed outside of the passage 416 of the sleeve 410 when the clip 420 is in the open configuration and when the clip 420 is in the closed configuration. As shown, the distal ends 434, 454 of the clip arms 430, 450 may move toward one another when the clip 420 is moved from the open configuration to the closed configuration, and the distal ends 434, 454 of the clip arms 430, 450 may move away from one another when the clip 420 is moved from the closed configuration to the open configuration. Various contours or profiles of the clip arms 430, 450, as shown in the views of FIGS. 4A and 4B, may be used in different embodiments. The contours or profiles of the clip arms 430, 450 may dictate how the clip arms 430, 450 move relative to each other and the sleeve 410 when the clip 420 is moved between the open configuration and the closed configuration. In some embodiments, the clip arms 430, 450 may engage one or more features of the sleeve 410 when the clip 420 is moved from the open configuration to the closed configuration and/or when the clip 420 is moved from the closed configuration to the open configuration, with the contours or profiles of the clip arms 430, 450 and/or the engaged features guiding movement of the clip arms 430, 450 relative to each other and the sleeve 410. In some instances, the clip arms 430, 450 additionally or alternatively may engage one or more features of other components of the device 400 (i.e., other than the sleeve 410) when the clip 420 is moved from the open configuration to the closed configuration and/or when the clip 420 is moved from the closed configuration to the open configuration, with the contours or profiles of the clip arms 430, 450 and/or the engaged features guiding movement of the clip arms 430, 450 relative to each other and the sleeve 410. According to various arrangements, each of the clip arms 430, 450 may include one or more straight segments (i.e., linear segments) having a straight profile and one or more curved segments (i.e., curvilinear segments) having a curved profile. As shown, each of the clip arms 430, 450 may include a plurality of straight segments and a plurality of curved segments, which define the overall contoured profiles of the clip arms 430, 450 for guiding movement of the clip arms 430, 450 relative to one another and the sleeve 410.

One or both of the clip arms 430, 450 may include one or more grasping features configured for engaging and grasping tissue of the gastrointestinal wall during use of the device 400. As shown, the first clip arm 430 may include a first needle 438 (which also may be referred to as a "first anchor" or a "first extension") configured for engaging and grasping tissue, and the second clip arm 450 may include a second needle 458 (which also may be referred to as a "second anchor" or a "second extension") configured for engaging and grasping tissue. As shown, the first needle 438 may extend to the distal end 434 of the first clip arm 430, and the second needle 458 may extend to the distal end 454 of the second clip arm 450. In this manner, the first needle 438 may define the distal end 434 of the first clip arm 430, and the second needle 458 may define the distal end 454 of the second clip arm 450. In some embodiments, as shown, at least a portion of each of the needles 438, 458 may have a curved shape. For example, a distal portion of each of the needles 438, 458 extending to the respective distal ends 434, 454 of the clip arms 430, 450 may have a curved shape, as shown. In some embodiments, an entirety of each of the needles 438, 458 may have a curved shape. In other embodiments, at least a portion of each of the needles 438, 458 may have a straight shape. For example, a distal portion of each of the needles 438, 458 extending to the respective distal ends 434, 454 of the clip arms 430 may have a straight shape. Various shapes of the needles 438, 458 may be used in different embodiments. In some embodiments, at least one, or both, of the needles 438, 458 may be configured for advancing through the mucosal layer and into at least the submucosal layer of the gastrointestinal wall. In some embodiments, at least one, or both, of the needles 438, 458 may be configured for advancing through the mucosal layer and the submucosal layer and into at least the muscularis layer of the gastrointestinal wall. In some embodiments, at least one, or both, of the needles 438, 458 may be configured for advancing through the mucosal layer, the submucosal layer, and the muscularis layer and into the serosal layer of the gastrointestinal wall. As shown, the distal tips of the needles 438, 458 may be pointed or otherwise sharpened to facilitate insertion of the needles 438, 458 into and through tissue. In some embodiments, the needles 438, 458 may include one or more retention features configured for retaining the needles 438, 458 within tissue into which the needles 438, 458 are inserted, thereby inhibiting or preventing removal of the needles 438, 458 from the engaged tissue. For example, at least one, or both, of needles 438, 458 may include one or more barbs, one or more serrations, or one or more other retention features, which may be spaced apart from the respective distal ends 434, 454 of the clip arms 430, 450. In some embodiments, as shown, both of needles 438, 458 may include an arrowhead tip 442, 462 disposed at the respective distal ends 434, 454 of the clip arms 430, 450 and configured for retaining the needles 438, 458 within engaged tissue. As discussed below, the needles 438, 458 may be used to facilitate closure of large defects as well as deep defects in the gastrointestinal wall.

FIGS. 4C and 4D illustrate an example use of the endoscopic clip device 400 for closure of a defect D in a gastrointestinal wall GW in accordance with embodiments of the present disclosure. The mucosal layer ML, the submucosal layer SML, the muscularis layer MSL, and the serosal layer SL of the gastrointestinal wall GW are shown in the figures. As shown, the defect D may be a mucosal defect extending into the mucosal layer ML of the gastrointestinal wall GW, without extending into the submucosal layer SML of the gastrointestinal wall GW. According to the illustrated example, the defect D may be a relatively small defect formed between a first margin FM and a second margin SM, with a width of the defect D between the first margin FM and the second margin SM being less than a distance between the distal ends 434, 454 of the clip arms 430, 450 when the clip 420 is in the open configuration. In other words, as shown in FIG. 4C, the clip 420 may be able to span the width of the defect D when the clip 420 is in the open configuration.

As discussed above, the device 400 may be advanced through an operative channel of an endoscope or an overtube which may have a tortuous shape according to a location of the defect D within the gastrointestinal tract. Using a delivery device, the device 400 may be advanced through the operative channel while the clip 420 is in the closed configuration. In some instances, while the device 400 is advanced through the operative channel, a sheath of the delivery device may extend over and beyond the distal ends 434, 456 of the clip arms 430, 450 to prevent contact between the clip 420 and the operative channel. The device 400 may be advanced out of the operative channel to a location near but spaced apart from the defect D while the clip 420 remains in the closed configuration. The sheath may be retracted to expose the device 400, and then the clip 420 may be moved from the closed configuration to the open configuration. With the clip 420 in the open configuration, the device 400 may be positioned relative to the defect D, the first needle 438 may be advanced into the first margin FM, and the second needle 458 may be advanced into the second margin SM, as shown in FIG. 4C. As shown, the first needle 438 may be advanced through the mucosal layer ML and into at least the submucosal layer SML, and the second needle 458 may be advanced into the mucosal layer ML. In different embodiments, the first needle 438 may be advanced into the muscularis layer MSL or into the serosal layer SL.

The clip 420 then may be moved to the closed configuration to approximate the first margin FM and the second margin SM, grasping the engaged mucosal tissue therebetween and closing the defect D, as shown in FIG. 4D. In some embodiments, as shown, as the clip 420 is moved from the open configuration to the closed configuration, the needles 438, 458 may be advanced deeper into the gastrointestinal wall GW. After achieving a suitable position of the device 400 relative to the defect D and desired engagement between the clip 420 and the mucosal tissue, the device 400 may be deployed from the delivery device. In some instances, a plurality of the devices 400 may be used for closure of the defect D, depending on its size, with each of the devices 400 being used to approximate respective portions of the margins FM, SM and thus provide closure of a respective portion of the defect D.

FIGS. 4E-4J illustrate another example use of the endoscopic clip device 400 for closure of a larger defect D in a gastrointestinal wall GW in accordance with embodiments of the present disclosure. The illustrated technique may be employed when the width of the defect D is greater than the distance between the distance between the distal ends 434, 454 of the clip arms 430, 450 when the clip 420 is in the open configuration. With the clip 420 in the open configuration, the first needle 438 may be advanced into the mucosal layer ML, as shown in FIG. 4E. The clip 420 then may be moved to the closed configuration, as shown in FIG. 4F. Next, as shown in FIG. 4G, the device 400 may be used to pull the first margin FM toward the second margin SM while the clip 420 is in the closed configuration, while the first needle 438 remains engaged with the first margin FM, thereby approximating the first margin FM and the second margin SM. With the first needle 438 positioned adjacent the second margin SM, the first needle 438 may be further advanced into the gastrointestinal wall GW to secure the margins FM, SM, as shown in FIG. 4H. In some embodiments, as shown, the first needle 438 may be advanced through the mucosal layer ML and into the submucosal layer SML. In different embodiments, the first needle 438 may be advanced into the muscularis layer MSL or into the serosal layer SL. Next, the clip 420 may be moved from the closed configuration to the open configuration, and the second needle 458 may be inserted into the second margin SM, as shown in FIG. 4I. As shown in FIG. 4J, the clip 420 then may be moved from the open configuration to the closed configuration such that the needles 438, 458 advance further into the tissue, engaging and grasping the tissue therebetween and securing closure of the defect D.

Although the example of FIGS. 4A and 4B and the example of FIGS. 4E-4J show the device 400 being used for closure of a mucosal defect, the device 400 may be used in a similar manner for closure of a defect D that extends deeper than the mucosal layer ML of the gastrointestinal wall GW. For example, when a defect D extends into the submucosal layer SML, the muscularis layer MSL, or the serosal layer SL, the deep engagement provided by the needles 438, 458 of the device 400 may provide approximation of the opposing margins FM, SM of the defect D along the deeper layers of the gastrointestinal wall GW. For these same reasons, in some embodiments, the device 400 also may be suitable for closure of a transmural perforation in the gastrointestinal wall GW.

Figure 5D:
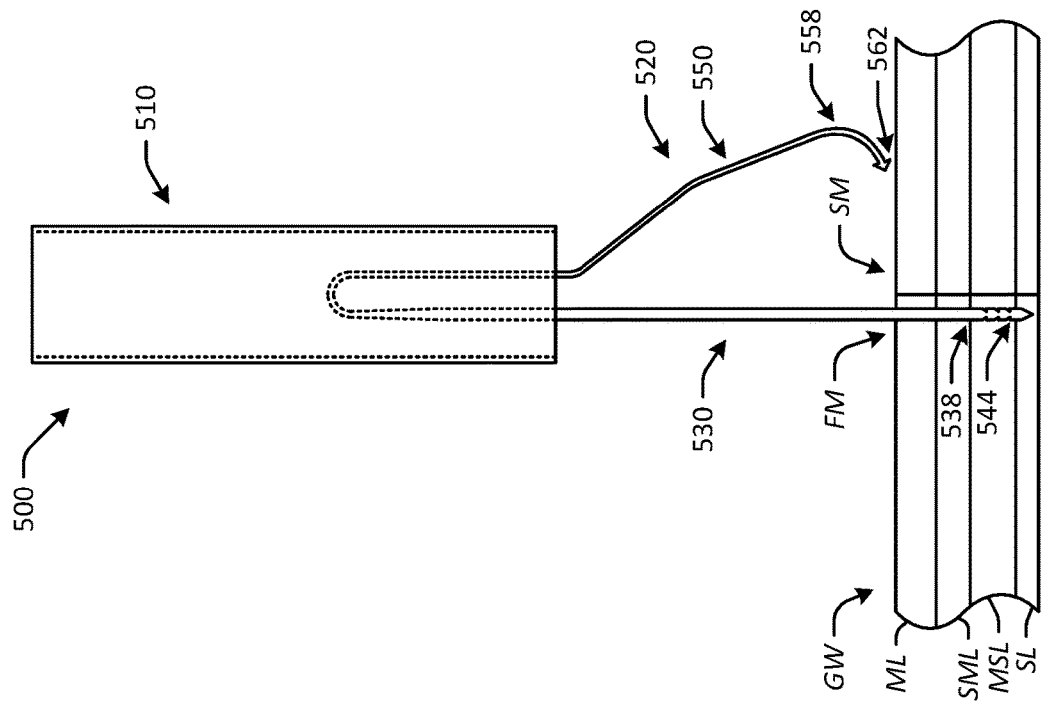
FIGS. 5C-5E are side views of the endoscopic clip device of FIG. 5A, illustrating an example method for closure of a transmural perforation in a gastrointestinal wall in accordance with embodiments of the disclosure.
Figure 5C:
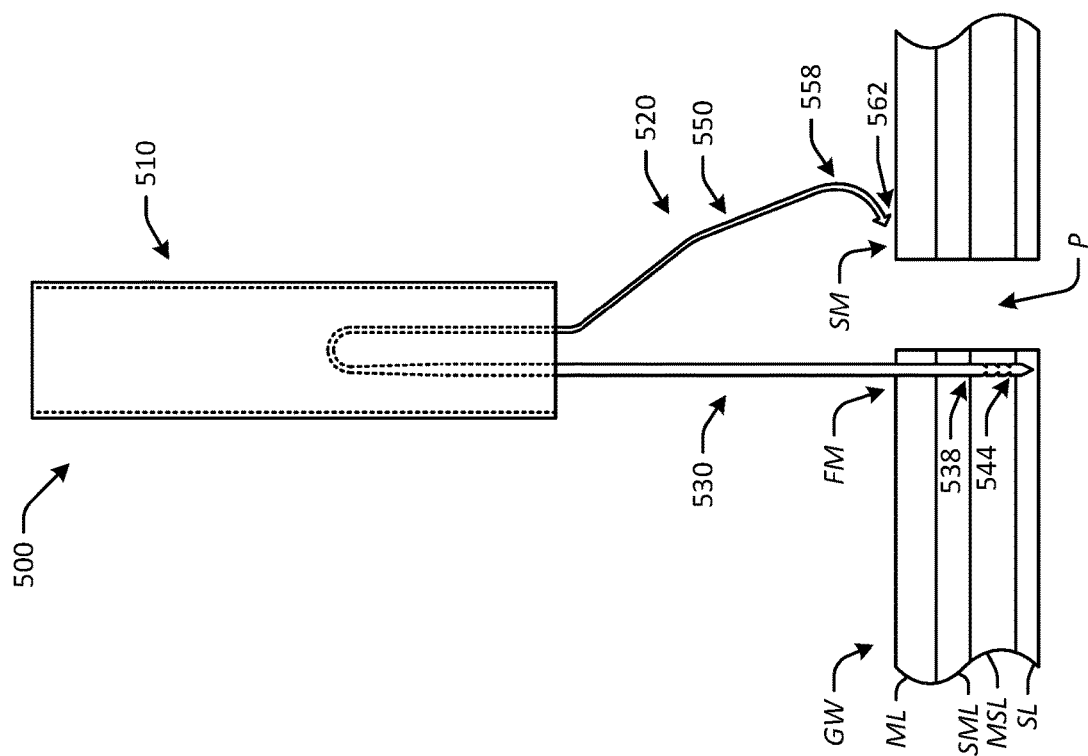
Figure 5E:
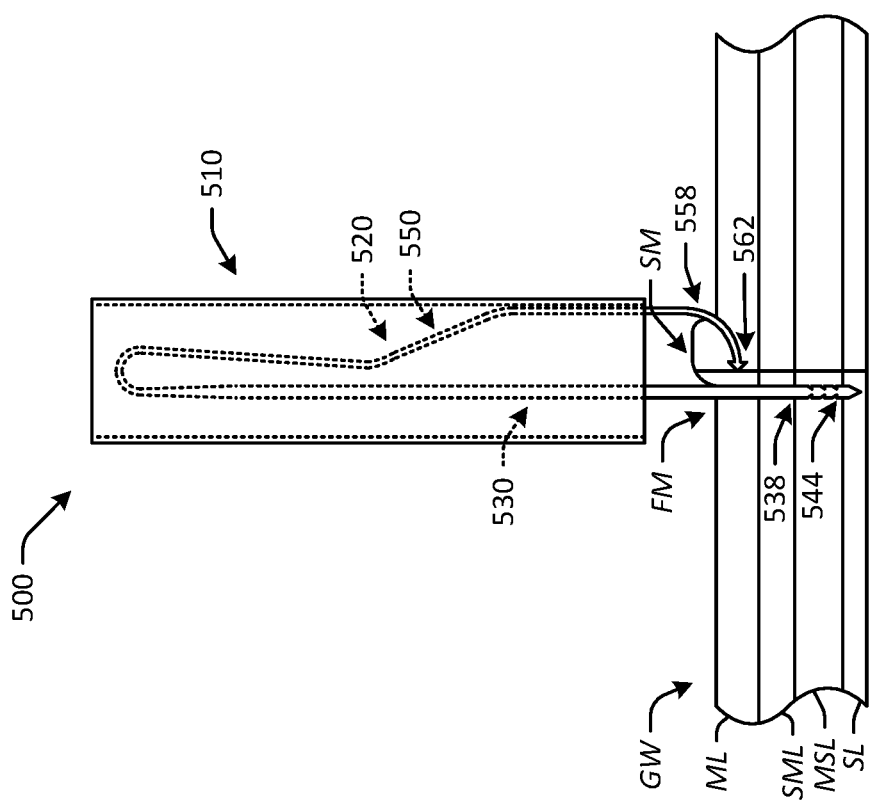

FIGS. 5A and 5B illustrate an example endoscopic clip device 500 (which also may be referred to as an "endoscopic device" or simply a "device") in accordance with embodiments of the present disclosure. The endoscopic clip device 500 may be configured to be advanced through an operative channel to a treatment site for closure of a defect, such as a mucosal defect, or a transmural perforation in a gastrointestinal wall of a patient. In some embodiments, the endoscopic clip device 500 may be advanced through an operative channel of an endoscope and thus may be considered to be a TTS clip device. In other embodiments, the endoscopic clip device 500 may be advanced through an operative channel of an overtube that is positioned over and used in conjunction with an endoscope and thus may not be considered to be a true "through-the-scope" clip device. FIGS. 5C-5E show the endoscopic clip device 500 being used for closure of a transmural perforation P in a gastrointestinal wall GW in accordance with embodiments of the present disclosure, as discussed further below.

According to the example of FIGS. 5A and 5B, the endoscopic clip device 500 generally may include a sleeve 510 (which also may be referred to as a "shell" or a "capsule") and a clip 520 (which also may be referred to as an "endoscopic clip"). It will be appreciated that, in some embodiments, the device 500 also may include additional components other than the sleeve 510 and the clip 520, such as components that guide, control, or inhibit movement of the clip 520 relative to the sleeve 510 and/or components that facilitate interaction between the clip 520 or the sleeve 510 and mating components or features of a delivery device used to advance the device 500 through an operative channel of an endoscope or an overtube and subsequently deploy the device 500 within a patient's gastrointestinal tract. For simplicity of illustration, only the sleeve 510 and the clip 520 are shown in FIGS. 5A and 5B.

As shown in FIGS. 5A and 5B, the sleeve 510 may be formed as an elongated structure having a proximal end 512 and a distal end 514 disposed opposite one another along a longitudinal axis LA of the device 500. The longitudinal axis of the sleeve 510 may be coaxial with the longitudinal axis LA of the device 500. As shown, the sleeve 510 may define a passage 516 therein. In some embodiments, the passage 516 may extend from the proximal end 512 to the distal end 514 of the sleeve 510. In some embodiments, the sleeve 510 or at least a portion thereof may be formed as a tube having a cylindrical shape, although other shapes and configurations of the sleeve 510 may be used in other embodiments.

The clip 520 may be disposed at least partially within the sleeve 510 and may be coupled to the sleeve 510. As shown, a proximal portion of the clip 520 may be disposed within the passage 516 of the sleeve 510. According to different embodiments, various components and mechanisms may be used for coupling the clip 520 to the sleeve 510. As shown, the clip 520 may be configured for moving relative to the sleeve 510 between different configurations. According to the illustrated example, the clip 520 may be configured for reversibly moving relative to the sleeve 510 between an open configuration, as shown in FIG. 5A, and a closed configuration, as shown in FIG. 5B. The closed configuration of the clip 520 may be used for advancing the device 500 through an operative channel of an endoscope or an overtube to a treatment site and also for closing a defect in a gastrointestinal wall. The open configuration of the clip 520 may be used for positioning the device 500 relative to the gastrointestinal wall and for engaging tissue of the gastrointestinal wall with features of the clip 520 prior to closing the defect. As shown, the clip 520 may be reversibly moved between the open configuration and the closed configuration by translating the sleeve 510 relative to the clip 520 or translating the clip 520 relative to the sleeve 510 in the direction of the longitudinal axis LA of the device 500.

As shown in FIGS. 5A and 5B, the clip 520 generally may include a first clip arm 530 and a second clip arm 550 disposed opposite one another. In some embodiments, as shown, the clip 520 may be asymmetric such that the first clip arm 530 and the second clip arm 550 are not mirror images of one another. As shown, the clip 520 may be asymmetric about a plane extending through the longitudinal axis LA of the device 500 and perpendicular to the views of FIGS. 5A and 5B. The first clip arm 530 may be formed as an elongated structure having a proximal end 532 and a distal end 534 disposed opposite one another in the direction of the longitudinal axis LA of the device 500. In a similar manner, the second clip arm 550 may be formed as an elongated structure having a proximal end 552 and a distal end 554 disposed opposite one another in the direction of the longitudinal axis LA of the device 500. As shown, the first clip arm 530 may have a first length between the proximal end 532 and the distal end 534 in the direction of the longitudinal axis LA of the device 500, and the second clip arm 550 may have a second length between the proximal end 552 and the distal end 554 in the direction of the longitudinal axis LA of the device 500. In some embodiments, as shown, the first length may be different from the second length when the clip 520 is in the open configuration and when the clip 520 is in the closed configuration. In some embodiments, as shown, the first length may be greater than the second length. In some embodiments, as shown, the proximal end 532 of the first clip arm 530 may be coupled to the proximal end 552 of the second clip arm 550. In some embodiments, as shown, the first clip arm 530 and the second clip arm 550 may be integrally formed with one another, with the proximal end 532 of the first clip arm 530 being directly coupled to the proximal end 552 of the second clip arm 550. In other embodiments, the first clip arm 530 and the second clip arm 550 may be coupled to one another by one or more additional portions or components of the clip 520 which are separately formed and attached to the clip arms 530, 550. Various arrangements of the clip arms 530, 550 and the overall clip 520 may be used in different embodiments.

As shown, the proximal ends 532, 552 of the clip arms 530, 550 may be disposed within the passage 516 of the sleeve 510 when the clip 520 is in the open configuration and when the clip 520 is in the closed configuration. In contrast, the distal ends 534, 554 of the clip arms 530, 550 may be disposed outside of the passage 516 of the sleeve 510 when the clip 520 is in the open configuration and when the clip 520 is in the closed configuration. As shown, the distal ends 534, 554 of the clip arms 530, 550 may move toward one another when the clip 520 is moved from the open configuration to the closed configuration, and the distal ends 534, 554 of the clip arms 530, 550 may move away from one another when the clip 520 is moved from the closed configuration to the open configuration. Various contours or profiles of the clip arms 530, 550, as shown in the views of FIGS. 5A and 5B, may be used in different embodiments. The contours or profiles of the clip arms 530, 550 may dictate how the clip arms 530, 550 move relative to each other and the sleeve 510 when the clip 520 is moved between the open configuration and the closed configuration. In some embodiments, one or both of the clip arms 530, 550 may engage one or more features of the sleeve 510 when the clip 520 is moved from the open configuration to the closed configuration and/or when the clip 520 is moved from the closed configuration to the open configuration, with the contours or profiles of the clip arms 530, 550 and/or the engaged features guiding movement of the clip arms 530, 550 relative to each other and the sleeve 510. In some instances, one or both of the clip arms 530, 550 additionally or alternatively may engage one or more features of other components of the device 500 (i.e., other than the sleeve 510) when the clip 520 is moved from the open configuration to the closed configuration and/or when the clip 520 is moved from the closed configuration to the open configuration, with the contours or profiles of the clip arms 530, 550 and/or the engaged features guiding movement of the clip arms 530, 550 relative to each other and the sleeve 510. According to various arrangements, one or both of the clip arms 530, 550 may include one or more straight segments (i.e., linear segments) having a straight profile and one or more curved segments (i.e., curvilinear segments) having a curved profile. As shown, the second clip arm 550 may include a plurality of straight segments and a plurality of curved segments, which define the overall contoured profile of the second clip arm 550 for guiding movement of the clip arms 550 relative to the first clip arm 530 and the sleeve 510.

One or both of the clip arms 530, 550 may include one or more grasping features configured for engaging and grasping tissue of the gastrointestinal wall during use of the device 500. As shown, the first clip arm 530 may include a first needle 538 (which also may be referred to as a "first anchor" or a "first extension") configured for engaging and grasping tissue, and the second clip arm 550 may include a second needle 558 (which also may be referred to as a "second anchor" or a "second extension") configured for engaging and grasping tissue. As shown, the first needle 538 may extend to the distal end 534 of the first clip arm 530, and the second needle 558 may extend to the distal end 554 of the second clip arm 550. In this manner, the first needle 538 may define the distal end 534 of the first clip arm 530, and the second needle 558 may define the distal end 554 of the second clip arm 550. In some embodiments, as shown, at least a portion of the second needle 558 may have a curved shape. For example, a distal portion of the second needle 558 extending to the distal ends 554 may have a curved shape, as shown. In some embodiments, as shown, an entirety of the first needle 538 may have a straight shape. In some embodiments, as shown, the first needle 538 may extend parallel to the longitudinal axis LA of the device 500. Various shapes of the needles 538, 558 may be used in different embodiments. In some embodiments, at least one, or both, of the needles 538, 558 may be configured for advancing through the mucosal layer and into at least the submucosal layer of the gastrointestinal wall. In some embodiments, at least one, or both, of the needles 538, 558 may be configured for advancing through the mucosal layer and the submucosal layer and into at least the muscularis layer of the gastrointestinal wall. In some embodiments, at least one, or both, of the needles 538, 558 may be configured for advancing through the mucosal layer, the submucosal layer, and the muscularis layer and into the serosal layer of the gastrointestinal wall. As shown, the distal tips of the needles 538, 558 may be pointed or otherwise sharpened to facilitate insertion of the needles 538, 558 into and through tissue. In some embodiments, the needles 538, 558 may include one or more retention features configured for retaining the needles 538, 558 within tissue into which the needles 538, 558 are inserted, thereby inhibiting or preventing removal of the needles 538, 558 from the engaged tissue. For example, at least one, or both, of needles 538, 558 may include one or more barbs, one or more serrations, or one or more other retention features, which may be spaced apart from the respective distal ends 534, 554 of the clip arms 530, 550. As shown, the first needle 538 may include a plurality of serrations 544 configured for retaining the first needle 538 within engaged tissue. In some embodiments, as shown, the second needle 558 may include an arrowhead tip 562 disposed at the distal end 554 and configured for retaining the second needle 558 within engaged tissue. As discussed below, the needles 538, 558 may be used to facilitate closure of large defects as well as deep defects and transmural perforations in the gastrointestinal wall.

FIGS. 5C and 5D illustrate an example use of the endoscopic clip device 500 for closure of a transmural perforation P in a gastrointestinal wall GW in accordance with embodiments of the present disclosure. The mucosal layer ML, the submucosal layer SML, the muscularis layer MSL, and the serosal layer SL of the gastrointestinal wall GW are shown in the figures. As shown, the transmural perforation P may be formed between a first margin FM and a second margin SM, with a width of the transmural perforation P between the first margin FM and the second margin SM being less than a distance between the distal ends 534, 554 of the clip arms 530, 550 when the clip 520 is in the open configuration. In other words, as shown in FIG. 5C, the clip 520 may be able to span the width of the defect D when the clip 520 is in the open configuration.

As discussed above, the device 500 may be advanced through an operative channel of an endoscope or an overtube which may have a tortuous shape according to a location of the transmural perforation P within the gastrointestinal tract. Using a delivery device, the device 400 may be advanced through the operative channel while the clip 520 is in the closed configuration. In some instances, while the device 500 is advanced through the operative channel, a sheath of the delivery device may extend over and beyond the distal ends 534, 556 of the clip arms 530, 550 to prevent contact between the clip 520 and the operative channel. The device 500 may be advanced out of the operative channel to a location near but spaced apart from the transmural perforation P while the clip 520 remains in the closed configuration. The sheath may be retracted to expose the device 500, and then the clip 520 may be moved from the closed configuration to the open configuration. With the clip 520 in the open configuration, the device 400 may be positioned relative to the transmural perforation P, and the first needle 538 may be advanced into the first margin FM, as shown in FIG. 5C. As shown, the first needle 538 may be advanced through the mucosal layer ML, the submucosal layer SML, and the muscularis layer MSL and into the serosal layer SL. Next, as shown in FIG. 5D, the device 500 may be used to pull the first margin FM toward the second margin SM while the clip 520 is in the open configuration, while the first needle 538 remains engaged with the first margin FM, thereby approximating the first margin FM and the second margin SM. As shown in FIG. 5E, the clip 520 then may be moved from the open configuration to the closed configuration such that the second needle 558 advances into the mucosal layer ML of the second margin SM, engaging and grasping the tissue therebetween and securing closure of the transmural perforation P.

Although the example of FIGS. 5C-5E shows the device 500 being used for closure of a transmural perforation P, the device 500 may be used in a manner similar to that described above for closure of a defect D in the gastrointestinal wall GW.

Although specific embodiments of the disclosure have been described, one of ordinary skill in the art will recognize that numerous other modifications and alternative embodiments are within the scope of the disclosure. For example, while various illustrative implementations and structures have been described in accordance with embodiments of the disclosure, one of ordinary skill in the art will appreciate that numerous other modifications to the illustrative implementations and structures described herein are also within the scope of this disclosure.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments.

What is claimed is:

1. An endoscopic clip device for closure of a mucosal defect or a transmural perforation in a gastrointestinal wall, the endoscopic clip device comprising:
    a sleeve; and
    a clip disposed at least partially within and coupled to the sleeve, the clip configured for reversibly moving relative to the sleeve between an open configuration for positioning relative to the gastrointestinal wall and a closed configuration for closing the mucosal defect or the transmural perforation, and the clip comprising:
        a first clip arm configured for engaging the mucosal layer and the submucosal layer of the gastrointestinal wall, the first clip arm comprising:
            a first needle extending to a distal end of the first clip arm and configured for advancing through the mucosal layer and into at least the submucosal layer of the gastrointestinal wall, the first needle having a sharp beveled distal tip; and
            a first claw spaced apart from the distal end of the first clip arm and extending transverse to the first needle, the first claw configured for engaging the mucosal layer of the gastrointestinal wall when the first needle extends through the mucosal layer and into at least the submucosal layer of the gastrointestinal wall, the first claw having a non-beveled distal tip;
        wherein the first needle extends distally beyond the first claw; and
        a second clip arm disposed opposite the first clip arm and configured for engaging the mucosal layer of the gastrointestinal wall;
        wherein the clip is asymmetric such that the first clip arm and the second clip arm are not mirror images of one another;
    wherein the endoscopic clip device is configured for advancing through an operative channel of an endoscope or an overtube having a tortuous shape.

2. The endoscopic clip device of claim 1, wherein the first clip arm has a first length extending from a proximal end of the first clip arm to the distal end of the first clip arm, wherein the second clip arm has a second length extending from a proximal end of the second clip arm to a distal end of the second clip arm, and wherein the first length is different from the second length.

3. The endoscopic clip device of claim 1, wherein the second clip arm comprises a second claw configured for engaging the mucosal layer of the gastrointestinal wall.

4. The endoscopic clip device of claim 3, wherein the second claw is disposed at a distal end of the second clip arm.

5. The endoscopic clip device of claim 3, wherein the second clip arm further comprises a second needle extending to a distal end of the second clip arm and configured for advancing through the mucosal layer and into at least the submucosal layer of the gastrointestinal wall, wherein the second claw is spaced apart from the distal end of the second clip arm and extends transverse to the second needle, and wherein the second claw is configured for engaging the mucosal layer of the gastrointestinal wall when the second needle extends through the mucosal layer and into at least the submucosal layer of the gastrointestinal wall.

6. The endoscopic clip device of claim 1, wherein the second clip arm comprises a second needle extending to a distal end of the second clip arm and configured for advancing into at least the mucosal layer of the gastrointestinal wall.

7. The endoscopic clip device of claim 6, wherein the first clip arm has a first length extending from a proximal end of the first clip arm to the distal end of the first clip arm, wherein the second clip arm has a second length extending from a proximal end of the second clip arm to a distal end of the second clip arm, and wherein the first length is different from the second length.

8. The endoscopic clip device of claim 6, wherein the first needle has a curved shape, and wherein the second needle has a curved shape.

9. The endoscopic clip device of claim 6, wherein the first needle has a straight shape extending parallel to or coaxial with a longitudinal axis of the sleeve and configured for extending parallel to or coaxial with a longitudinal axis of the operative channel, and wherein the second needle has a curved shape.

10. The endoscopic clip device of claim 6, wherein the first needle comprises a first arrowhead tip disposed at the distal end of the first clip arm, and wherein the second needle comprises a second arrowhead tip disposed at the distal end of the second clip arm.

11. The endoscopic clip device of claim 6, wherein the first needle comprises a plurality of barbs spaced apart from the distal end of the first clip arm.

12. The endoscopic clip device of claim 6, wherein the first needle comprises a plurality of serrations spaced apart from the distal end of the first clip arm.

13. The endoscopic clip device of claim 6, wherein the second needle is configured for advancing through the mucosal layer and into at least the submucosal layer of the gastrointestinal wall.

14. A method of using an endoscopic clip device for closure of a mucosal defect or a transmural perforation in a gastrointestinal wall, the method comprising:
    advancing the endoscopic clip device through an operative channel of an endoscope or an overtube having a tortuous shape, the endoscopic clip device comprising:
        a sleeve; and
        a clip disposed at least partially within and coupled to the sleeve, the clip configured for reversibly moving relative to the sleeve between an open configuration and a closed configuration, and the clip comprising:
            a first clip arm comprising:
                a first needle extending to a distal end of the first clip arm;
                the first needle having a sharp beveled distal tip; and a first claw spaced apart from the distal end of the first clip arm and extending transverse to the first needle, the first claw having a non-beveled distal tip;

wherein the first needle extends distally beyond the first claw; and a second clip arm disposed opposite the first clip arm;

wherein the clip is asymmetric such that the first clip arm and the second clip arm are not mirror images of one another;

positioning the clip relative to the gastrointestinal wall while the clip is in the open configuration;

engaging a first margin along the mucosal defect or the transmural perforation with the first clip arm by advancing the first needle into at least the mucosal layer of the gastrointestinal wall;

pulling the first margin toward a second margin along the mucosal defect or the transmural perforation;

advancing the first needle into at least the submucosal layer of the gastrointestinal wall;

engaging the second margin with the second clip arm by engaging the mucosal layer of the gastrointestinal wall; and moving the clip from the open configuration to the closed configuration such that the first margin and the second margin are approximated in a linear manner.

15. The method of claim 14, further comprising, after engaging the first margin with the first clip arm by advancing the first needle into at least the mucosal layer of the gastrointestinal wall, moving the clip from the open configuration to the closed configuration, wherein pulling the first margin toward the second margin comprises pulling the first margin toward the second margin while the clip is in the closed configuration, and wherein advancing the first needle into at least the submucosal layer of the gastrointestinal wall comprises advancing the first needle into at least the submucosal layer of the gastrointestinal wall while the clip is in the closed configuration.

16. The method of claim 15, wherein advancing the first needle into at least the submucosal layer of the gastrointestinal wall comprises advancing the first needle into at least the submucosal layer of the gastrointestinal wall near the second margin.

17. The method of claim 15, further comprising, after advancing the first needle into at least the submucosal layer of the gastrointestinal wall, moving the clip from the closed configuration to the open configuration, wherein engaging the second margin with the second clip arm comprises engaging the second margin with the second clip arm while the clip is in the open configuration.

18. The method of claim 14, wherein the second clip arm comprises a second needle extending to a distal end of the second clip arm, and wherein engaging the second margin with the second clip arm comprises advancing the second needle into at least the mucosal layer of the gastrointestinal wall.

* * * * *